United States Patent
Howell et al.

(10) Patent No.: US 11,890,422 B2
(45) Date of Patent: Feb. 6, 2024

(54) ANESTHETIC NERVE BLOCK AND METHOD

(71) Applicant: PFOF LLC, Clearwater, FL (US)

(72) Inventors: Howard L. Howell, Clearwater, FL (US); Ralf Blackstone, Clearwater, FL (US)

(73) Assignee: PFOF LLC, Clearwater, FL (US)

( * ) Notice: Subject to any disclaimer, the term of this patent is extended or adjusted under 35 U.S.C. 154(b) by 0 days.

(21) Appl. No.: 18/144,043

(22) Filed: May 5, 2023

(65) Prior Publication Data
US 2023/0355916 A1    Nov. 9, 2023

Related U.S. Application Data

(60) Provisional application No. 63/439,780, filed on Jan. 18, 2023, provisional application No. 63/338,504, filed on May 5, 2022.

(51) Int. Cl.
*A61M 19/00* (2006.01)
*A61M 5/19* (2006.01)
(Continued)

(52) U.S. Cl.
CPC ........... *A61M 19/00* (2013.01); *A61K 31/167* (2013.01); *A61K 31/245* (2013.01);
(Continued)

(58) Field of Classification Search
CPC ...... A61M 19/00; A61M 5/1408; A61M 5/19; A61M 2205/15; A61M 5/00;
(Continued)

(56) References Cited

U.S. PATENT DOCUMENTS

| 4,695,576 A | 9/1987 | af Ekenstam et al. |
| 5,192,527 A | 3/1993 | Abrahmsohn |

(Continued)

FOREIGN PATENT DOCUMENTS

WO    WO 1996/028426    9/1996

OTHER PUBLICATIONS

Racle, Effect of Adding Sodium Bicarbonate to Bupivacaine for Spinal Anesthesia in Elderly Patients, International Anesthesia Research Society, 1988. 570-573.1988:67:570-3.

(Continued)

*Primary Examiner* — Jason E Flick
(74) *Attorney, Agent, or Firm* — Frijouf, Rust & Pyle, P.A.

(57) ABSTRACT

An improved anesthetic nerve block and method is disclosed comprising a dispenser including a storage body, a transfer body and a tip for positioning adjacent to the nerve. A local short acting anesthetic is in the storage body. A physiologic carbonate base is in the storage body. The local short acting anesthetic and the physiologic carbonate base are dispensed from the tip of the dispenser where the local short acting anesthetic facilities the penetration of the physiologic carbonate base through the nerve membrane and into the axon. A local long acting anesthetic is in the storage body. The local long acting anesthetic is dispensed from the tip of the dispenser and penetrates through the nerve membrane and into the axon. The local long acting anesthetic and the physiologic carbonate base cause a precipitate and form a crystallization compound for creating a prolonged local nerve block.

22 Claims, 14 Drawing Sheets

(51) Int. Cl.
  *A61M 5/14*    (2006.01)
  *A61K 31/445*  (2006.01)
  *A61K 31/245*  (2006.01)
  *A61K 47/02*   (2006.01)
  *A61K 31/167*  (2006.01)

(52) U.S. Cl.
  CPC ............ *A61K 31/445* (2013.01); *A61K 47/02* (2013.01); *A61M 5/1408* (2013.01); *A61M 5/19* (2013.01); *A61M 2205/05* (2013.01)

(58) Field of Classification Search
  CPC .. A61M 5/1407; A61M 5/1409; A61M 5/178; A61M 2005/1787; A61K 31/167; A61K 31/245; A61K 31/445; A61K 47/02; A61K 31/00; A61K 47/00
  See application file for complete search history.

(56) References Cited

U.S. PATENT DOCUMENTS

| | | | |
|---|---|---|---|
| 5,425,707 A * | 6/1995 | Goldberg | A61B 17/320036 604/506 |
| 5,777,124 A | 7/1998 | Zavareh et al. | |
| 5,849,763 A | 12/1998 | Bardsley et al. | |
| 5,919,804 A | 7/1999 | Gennery | |
| 5,945,435 A | 8/1999 | Evetts | |
| 5,955,479 A | 9/1999 | Bardsley et al. | |
| 6,019,994 A | 2/2000 | Evetts et al. | |
| 6,069,155 A | 5/2000 | Mather et al. | |
| 6,156,900 A | 12/2000 | Dyer et al. | |
| 8,828,452 B2 | 9/2014 | Abrahmsohn | |
| 2017/0157082 A1 * | 6/2017 | Poulsen | A61K 45/06 |

OTHER PUBLICATIONS

Hwang, Crystallization of Local Anesthetics When Mixed With Corticosteroid Solutions, Annals of Rehabilitation Medicine, 2016;40(1):21-27.
Brandis, Alkalinisation of local anaesthetic solutions, www.australianprescriber.com. Australian Prescriber, vol. 34, No. 6. Dec. 2011.
Marwoto, Onset response of bupivacaine 0.5% which has been added with sodium bicarbonate on epidural block, Department of Anesthesiology, University of Diponegoro, vol. 14,No. 1,2005.
Bedforth, Bicarbonate causing precipitation in epidural top-up solutions, Anaesthesia, 2010, 65, p. 960, UK.
Donchin, Effect of Sodium Bicarbonate On the Kinetics of Bupivacaine in I.V. Regional Anaesthesia in Dogs, British Journal of Anaesthesia, (1980). 52, 969-974.
McMorland, The effect of pH adjustment of bupivacaine on onset and duration of epidural anaesthesia for Caesarean section, Canadian Journal of Anaesthesia, 1988/35:5/457-461.
Choi, Non-Particulate Steroids Combined with Local Anesthetics A Potentially Unsafe Mixture, Journal of Pain Research 2021:14 1495-1504.
Neal, Checklist for Treatmentof Local Anesthetic Systemic Toxicity, American Society Ofregional Anesthesia and Pain Medicine, ASRAPM-Checklist.indd 2011.
Oda, Pharmacokinetics and systemic toxicity of local anesthetics in children, Japanese Society of Anesthesiologists, (2016) 30:547-550.
Best, Buffered lidocaine and bupivacaine mixture -the ideal local anesthetic solution?, Canadian Society of Plastic Surgeons, Plast Surg vol. 23 No 2 Summer 2015, 87-90.
Hoerner, Crystallization of ropivacaine and bupivacaine when mixed with different adjuvants, Reg Anesth Pain Med 2022;47:625-629. doi:10.1136/rapm-2022-103610.
Yung, Bicarbonate Plus Epinephrine Shortens the Onset and Prolongs the .... Regional Anesthesia and Pain Medicine; May/Jun. 2009: 34, 3; Nursing & Allied Health Database p. 196.
Peterfreund, pH Adjustment of Local Anesthetic Solutions with Sodium Bicarbonate .. , Regional Anesthesia - Nov Dec. 1989, vol. 14 No. 6 pp. 265-270.
Ikuta, pH Adjustment Schedule for the Amide Local Anesthetics, Regional Anesthesia - Sept Oct. 1989, vol. 14 No. 5 pp. 229-235.
Koitabashi, Changing compatibility by temperature of local anesthetics with sodium bicarbonate, 1996, Matsui, PMID 8721130, JP.
Koitabashi, Precipitation of pH-adusted local anesthetics with soduim bicarbonate, Anesthesia, vol. 44, No. 1, Jan. 1995 JP.
Heinonen, The current status of local anesthesia in anaesthesiology, , Duodecim, 1967: 83: pp. 1176-1183.

* cited by examiner

Direction of Nerve Impulse (A-delta Nerve Fiber)

ALALAC block sequence with options
created by any administration device

STAGE 1 - "test dose" and pimary nerve block

Lidocaine + NaHCO3:Na2CO3:NaOH bases
+ Epinephrine
possible Precipitating Steroid
possible dexmedetomidine
adjuvants must be stable in
an alkaline environment → Injection perineurally
Lidocaine + NaHCO3:Na2CO3:NaOH = unionized local anesthetic which penetrates neuron readily and raises pH inside neuron/axon.

STAGE 2    Mandatory 2-minute wait
Listening for tachycardia on pulse oximeter caused by intravascular epinephrine inadvertently injected- if epinephrine leaks intravascular, pulse will increase to 115% of baseline pulse or more- if this occurs, block at this level is immmediately abandoned.

STAGE 3    Saline injection through needle cleaning it sufficiently to render needle lumen a pH of 7.4 or lower- prevents crytallization inside the lumen of the needle upon injection of ALALA in Stage 4.

STAGE 4    Inject ALALA (ropivacaine, bupivacaine, levobupivacaine, tetraciane) to form ALALA crystals intraneurally and perineurally. Epinephrine included in this mixture to exclude intavascular penetration that could cause LAST (epinephrine = vascular marker).

FIG. 23

Alternate Protocol for the Creation of the ALALA-Preciopitate Nerve Block
Alternate ALALA block sequence with
options created by any administration device

STAGE 1 - the "test dose"

Lidocaine + Epinephrine
plus possible Precipitating Steroid
possible dexmedetomidine
or other a²-agonist, NSAID, NMDA
antagonist, μ²-agonist Injection perineurally
Lidocaine will set up a nerve block while
the epinephrine tests for intravascular
connection that could represent a danger
to the patient if an ALALA drug is injected

STAGE 2 — Mandatory 2-minute wait for reaction to the test dose
Listening for tachycardia on pulse oximeter caused by intravascular epinephrine inadvertently injected - if epinephrine leaks intravascular, pulse will increase to 115% of baseline pulse or more - if this occurs, block at this level is immmediately abandoned.

STAGE 3 — Inject ALALA (ropivacaine, bupivacaine, levobupivacaine) drug(s). Adjuvants not stable in Stage 1 may be included here, including in the mixture dexmedetomdine or other a²-agonist, NSAID, NMDA antagonist, μ²-agonist, can be injected here *except* precipitating steroids as these can precipitate the mixture before injection, and so interfere with injection.

STAGE 4 — Saline injection through needle cleaning it sufficently to render needle lumen a pH of 7.4 or lower - prevents precipitation/crytallization inside the lumen of the needle upon injection of base(s) in Stage 5.

STAGE 5 — Inject precipitating physiologic base(s) and precipitating steroid(s) through the unmoved injection needle to throughly mix with the ALALA drug(s) and adjuvant(s) above. This dose of precipitating physiologic base(s) and steroid(s) is pre-calculated to raise the pH of this combined mixture to an optimal pH to produce the neural block of the desired duration. Final mixture should be in the physiologic range (ph 7.4-8.4) so as not to cause tissue damage perineurally due to excessive pH.

FIG. 24

ANESTHETIC NERVE BLOCK AND METHOD

CROSS-REFERENCE TO RELATED APPLICATIONS

This application claims benefit of U.S. Patent Provisional application No. 63/338,504 filed May 5, 2022. All subject matter set forth in provisional application No. 63/338,504 is hereby incorporated by reference into the present application as if fully set forth herein.

This application claims benefit of U.S. Patent Provisional application No. 63/439,780 filed Jan. 18, 2023. All subject matter set forth in provisional application No. 63/439,780 is hereby incorporated by reference into the present application as if fully set forth herein.

BACKGROUND OF THE INVENTION

Field of the Invention

This invention relates to the pain relief and more particularly, this invention relates to an improved anesthetic nerve block and method.

Background of the Invention

Recognizing opioid prescriptions are a major gateway to opioid addiction with more than 350,000 deaths due to opioid overdoses worldwide. This invention shows how to replace opioids for pain relief with nerve blocks lasting for days which could replace the need for opioid drugs after surgery and trauma.

The recent opioid crisis has focused world attention on the need to provide non-addictive post operative pain relief for patients after surgery, trauma, and other painful occurrences. The large number of peripheral nerve blocks (PNB's) by anesthesiologists illustrates our recognition of the utility and effectiveness of such nerve blocks in the treatment of pain without the need for addictive opioid drugs.

Pain studies have indicated sharp pain (A-delta pain fibers) largely subsides in 48 hours after uncomplicated abdominal surgery. Even inflammatory diffuse pain (C-pain fibers) is mostly subsided after 120 hours in such surgeries. Thus, the requirement for a post-operative analgesic capable of lasting 120 hours as elimination of the need for opioid prescriptions is the goal.

Unfortunately, such post-operative analgesia by PNB's has classically been limited to 24 hours or less, depending on the local anesthetic selected for the block. Inclusion of alpha-2 agonists (clonidine, dexmedetomidine, etc.), steroids, and even epinephrine have been used to prolong these blocks, though only just longer than that achieved by local anesthetics alone. Even with the longest-acting local anesthetics with multiple adjuvants, effective analgesia rarely lasts more than 24 hours in peripheral nerve blocks. The following patents and publications are representative of attempts of the prior art to advance the trigger pump art.

U.S. Pat. No. 4,695,576 to Ekenstam discloses a local anesthetic, L-N-n-propylpipecolic acid-2,6-xylidide, is prepared by chlorinating L-pipecolic acid to yield the acid chloride, namely L-pipecolic acid chloride. The acid chloride is then reacted with 2,6-xylidine to yield L-pipecolic acid-2,6-xylidide. The L-N-pipecolic acid-2,6-xylidide is then propylated to yield the L-N-n-propylpipecolic acid-2,6-xylidide, which is a potent local anesthetic for humans and is of relatively low toxicity.

U.S. Pat. No. 5,192,527 to Abrahmsohn discloses a method of controlling the duration of local anesthesia and a reagent system or kit for inducing and limiting the duration of local anesthesia is described.

U.S. Pat. No. 5,777,124 to Zavareh et al. discloses a process for preparing levobupivacaine, racemic bupivacaine or another N-alkyl analogue thereof, comprises chlorinating pipecolic acid hydrochloride, amidation of the resultant pipecolyl chloride hydrochloride in solvent, without isolation, with 2,6-dimethylaniline, and alkylation of the resultant pipecolic acid 2,6-xylidide. Alternatively, the alkylation may be followed by the amidation.

U.S. Pat. No. 5,849,763 to Bardsley et al. discloses levobupivacaine ((S)-1-butyl-N-(2,6-dimethylphenyl)-2-piperidinecarboxamide) useful as an anesthetic, particularly in a patient who is CNS-compromised or predisposed to CNS side-effects. It is also useful as an anesthetic in obstetrics.

U.S. Pat. No. 5,919,804 to Gennery discloses levobupivacaine used for providing anesthesia or analgesia in a human patient in and after facial surgery, especially in dentistry or ophthalmics.

U.S. Pat. No. 5,945,435 to Evetts discloses levobupivacaine particularly suitable for use in anaesthetising a human patient prior to surgery that does not require hospitalisation for more than 12 hours after loss of motor block. Because of its beneficial motor block/sensory block characteristics, levobupivacaine can be used for 'daycare' surgery.

U.S. Pat. No. 5,955,479 to Bardsley et al. discloses use of levobupivacaine for the treatment of chronic pain in a patient. Levobupivacaine used in the subject methods is substantially free of dexbupivacaine. The methods of the invention can be used, for example, to treat pain in patients that are cardiac compromised, suffering from central nervous system damage or cancer.

U.S. Pat. No. 6,019,994 to Evetts et al. discloses levobupivacaine or ropavicaine used to treat migraine.

U.S. Pat. No. 6,069,155 to Mather et al. discloses a method of anesthetizing a human patient prior to major surgery, which comprises the administration to the patient of at least 200 mg levobupivacaine.

U.S. Pat. No. 6,156,900 to Dyer et al. discloses a process for the preparation of optically-enriched pipecolic acid as a salt with an optically-active acid, comprises asymmetric transformation of pipecolic acid, as a racemic mixture of a mixture enriched in the opposite enantiomer from that desired, with the optically-active acid in a solvent comprising an acid that causes racemisation, in the absence of aldehyde.

U.S. Pat. No. 8,828,452 to Abrahmsohn discloses methods for providing post-operative pain control or relief to a patient are disclosed. Methods include, for example, administering bicarbonate to an area of a patient during a surgical or dental procedure, near completion of a surgical or dental procedure or immediately following a surgical or dental procedure, in an area previously administered or containing a regional or local anesthetic in an amount sufficient to provide the patient with pain control or relief for a period of time after the surgical or dental procedure.

WO 1996/028426 to Dyer et al. discloses an optically-enriched N,O-dialkyl pipecolates are useful in the preparation of levobupivacaine and related analgesics. They may be prepared simply by dialkylating optically-enriched pipecolic acid by reaction with an alkylating agent, in the presence of base and a polar aprotic solvent.

Although the forgoing patents have contributed to the advancement of the prior art, there is still a need for a long-lasting local anesthetic capable of providing post-surgical and post-traumatic analgesia of 120 hours or more, thereby greatly diminishing the need for opioid prescriptions for these occurrences.

Therefore, it is an object of the present invention to provide an improved anesthetic nerve block that provides a substantial advancement to the art.

Another object of the present invention is to provide an improved anesthetic nerve block that may be quickly dispensed.

Another object of the present invention is to provide an improved anesthetic nerve block that may be easily dispensed.

Another object of the present invention is to provide an improved anesthetic nerve block that may be dispensed into a living organism with a low risk of harm.

Another object of the present invention is to provide an improved anesthetic nerve block that may be altered to vary the time duration of the nerve block.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention and the detailed description describing the preferred embodiment of the invention.

SUMMARY OF THE INVENTION

The present invention is defined by the appended claims with the specific embodiments shown in the attached drawings. For the purpose of summarizing the invention, the invention comprises an improved anesthetic nerve block for interrupting the electrical potential of a nerve and relieving pain within a living organism. The nerve has an axon covered by a nerve membrane. The anesthetic nerve block comprises a dispenser including a storage body, a transfer body and a tip for positioning adjacent to the nerve. A local short acting anesthetic is in the storage body. A physiologic carbonate base is in the storage body. The local short acting anesthetic and the physiologic carbonate base are dispensed from the tip of the dispenser where the local short acting anesthetic facilities the penetration of the physiologic carbonate base through the nerve membrane and into the axon. A local long acting anesthetic is in the storage body. The local long acting anesthetic is dispensed from the tip of the dispenser and penetrates through the nerve membrane and into the axon. The local long acting anesthetic and the physiologic carbonate base cause a precipitate and forming a crystallization compound for creating a prolonged local nerve block.

In one embodiment of the invention, the local short acting anesthetic is lidocaine.

In another embodiment of the invention, the local long acting anesthetic is selected from the group consisting of bupivacaine, levo-bupivacaine, ropivacaine and tetracaine.

In another embodiment of the invention, the physiologic carbonate base is selected from the group consisting of sodium bicarbonate, sodium carbonate and sodium hydroxide.

In another embodiment of the invention, the local short acting anesthetic is in the storage body. A steroid is in the storage body. The local short acting anesthetic and the steroid are dispensed from the tip of the dispenser where the local short acting anesthetic facilities the penetration of the steroid through the nerve membrane and into the axon. A local long acting anesthetic is in the storage body. The local long acting anesthetic is dispensed from the tip of the dispenser and penetrates through the nerve membrane and into the axon. The local long acting anesthetic and the steroid cause a precipitate and forming a crystallization compound for creating a prolonged local nerve block.

In another embodiment of the invention, the steroid base is selected from the group consisting of dexa-methasone, beta-methasone and triamcinolone.

The present invention further comprises a method for creating an anesthetic nerve block. The anesthetic nerve block interrupts the electrical potential of a nerve and relieves pain within a living organism. The nerve has an axon covered by a nerve membrane. The method comprising the steps of dispensing a local short acting anesthetic from a dispenser for positioning the local short acting anesthetic adjacent to the nerve. A physiologic carbonate base is dispensed from a dispenser for positioning the physiologic carbonate base adjacent to the nerve where the local short acting anesthetic facilities the penetration of the physiologic carbonate base through the nerve membrane and into the axon. A local long acting anesthetic is dispensed from a dispenser for positioning the local long acting anesthetic adjacent to the nerve where the local long acting anesthetic penetrates through the nerve membrane and into the axon and the local long acting anesthetic and the physiologic carbonate base cause a precipitate and form a crystallization compound for creating a prolonged local nerve block.

In another embodiment of the invention, the method comprises the steps of dispensing a local short acting anesthetic from a dispenser for positioning the local short acting anesthetic adjacent to the nerve. A local long acting anesthetic is dispensed from a dispenser for positioning the local long acting anesthetic adjacent to the nerve. A physiologic carbonate base is dispensed from a dispenser for positioning the physiologic carbonate base adjacent to the nerve where the local short acting anesthetic facilities the penetration of the physiologic carbonate base through the nerve membrane and into the axon and where the local long acting anesthetic penetrates through the nerve membrane and into the axon and the local long acting anesthetic and the physiologic carbonate base cause a precipitate and form a crystallization compound for creating a prolonged local nerve block.

The foregoing has outlined rather broadly the more pertinent and important features of the present invention in order that the detailed description that follows may be better understood so that the present contribution to the art can be more fully appreciated. Additional features of the invention will be described hereinafter which form the subject matter of the invention. It should be appreciated by those skilled in the art that the conception and the specific embodiments may be modified for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which:

FIG. 23 is a flow diagram of the first method for dispensing the anesthetic nerve block solution; and FIG. 24 is a flow diagram of the second method for dispensing the anesthetic nerve block solution.

Similar reference characters refer to similar parts throughout the several Figures of the drawings.

DETAILED DISCUSSION

FIGS. 1-24 illustrate an improved anesthetic nerve block and method. With reference to FIGS. 1-9, a peripheral stimulus 58, such as a pinprick to an arm or leg, must travel down its associated nerve to connect at the spinal cord before it can be transmitted to the brain where that pinprick is perceived. This transmission of the nerve electrical impulse from the periphery to the brain is achieved by the depolarization of the sodium/potassium potentials 56 across the nerve membrane (axolemma) 54 in the axon 24. These action potentials 56 in nerve firings flow as a result of sequential depolarization down the nerve fiber from periphery to spinal cord in the conduction of a nerve impulse.

Figure 1:
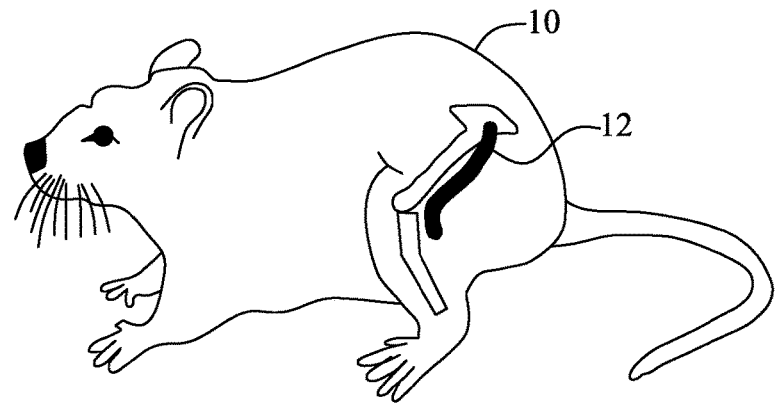
FIG. 1 is side view of a living organism having a sciatic nerve where an anesthetic nerve block solution is to be used for relieving pain.
Figure 2:
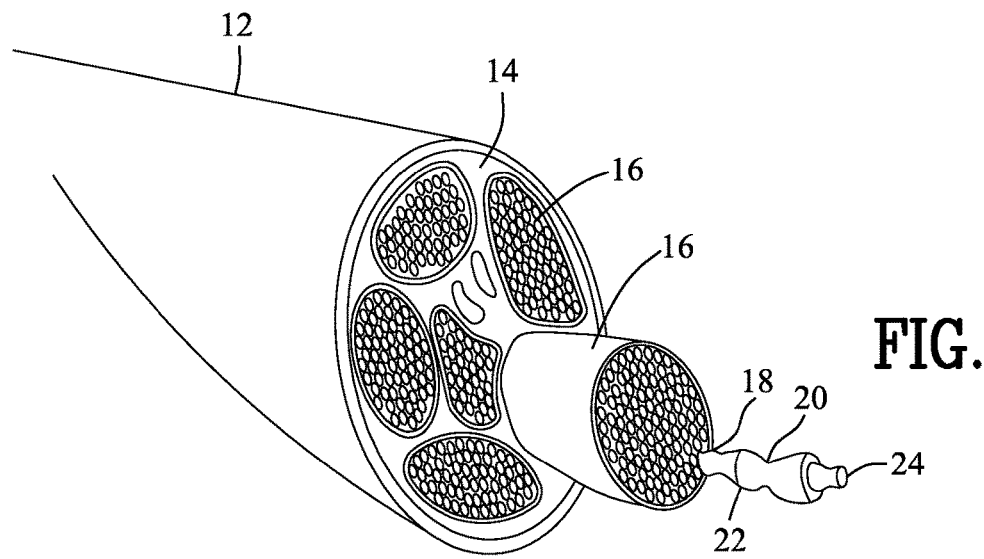
FIG. 2 is an enlarged sectional view of the sciatic nerve of FIG. 1.
Figure 3:
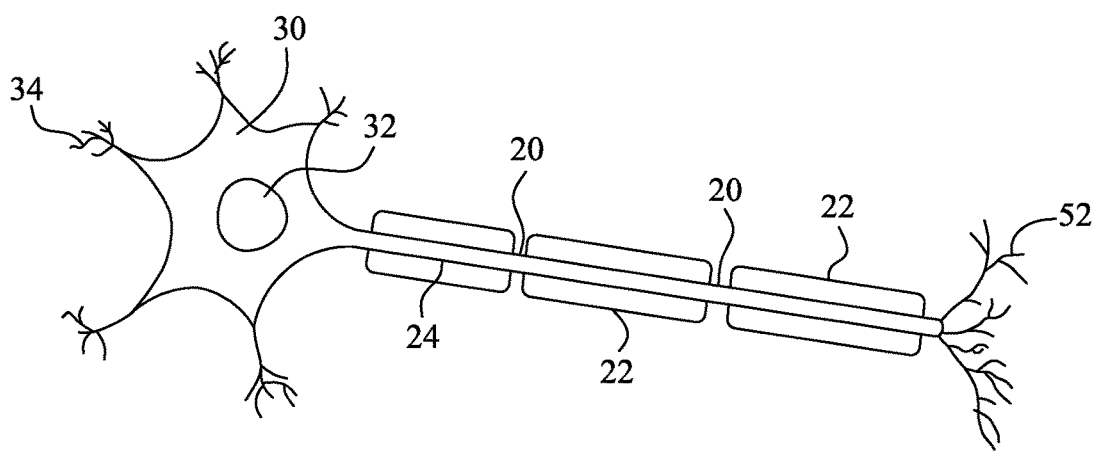
FIG. 3 is an enlarged portion of FIG. 2.
Figure 4:
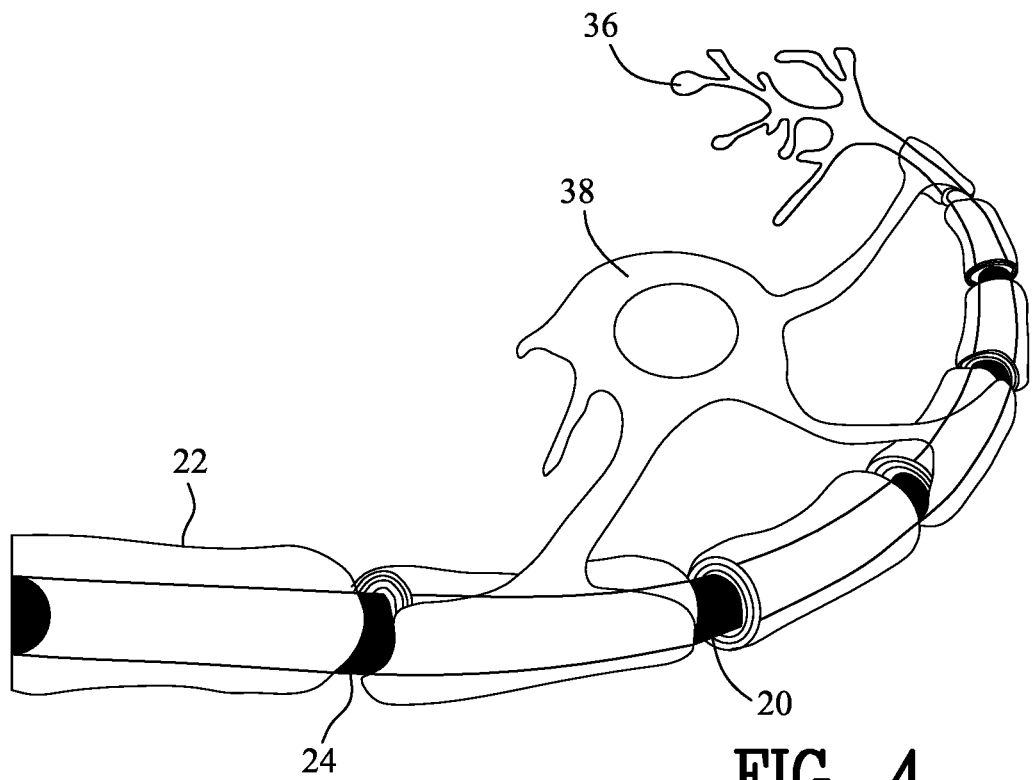
FIG. 4 is an isometric view of FIG. 3.
Figure 5:
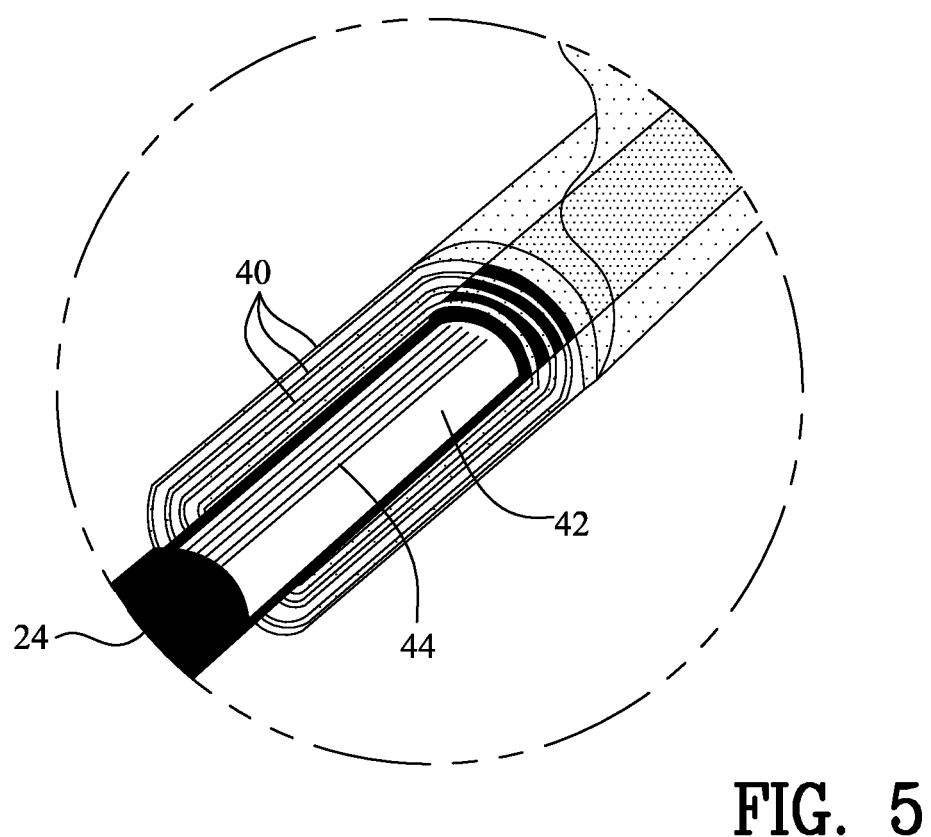
FIG. 5 is a sectional view of FIG. 4.
Figure 6:
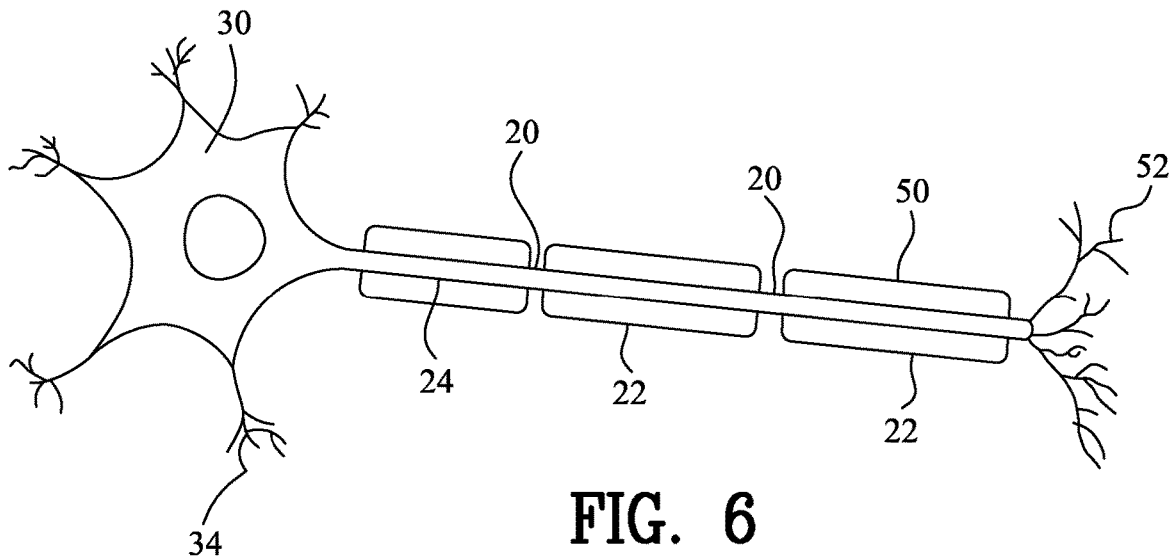
FIG. 6 is a view similar to FIG. 3 illustrating a myelinated neuron (A-delta fiber)
Figure 7:
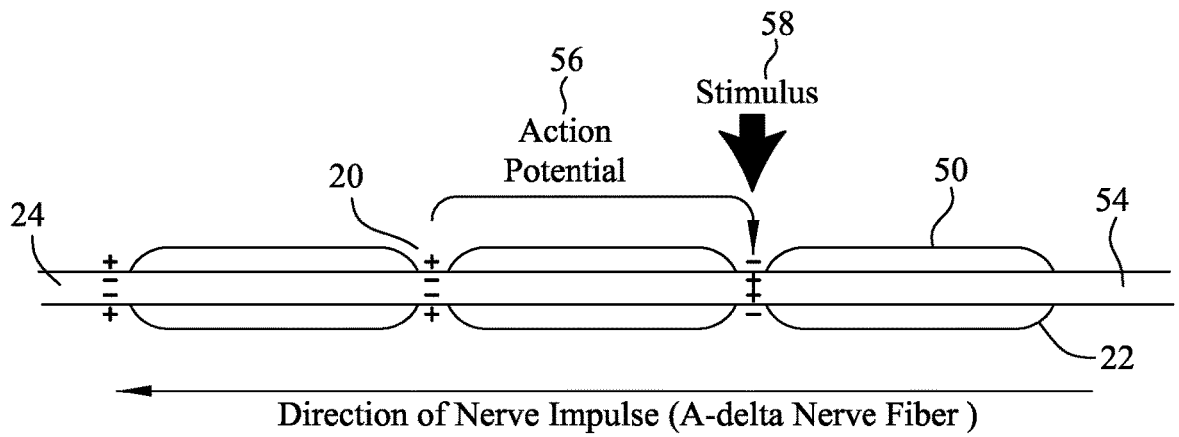
FIG. 7 is an enlarged portion of FIG. 6.

Such depolarizations may flow from one node of Ranvier 20 to the next in myelinated nerve fibers, as illustrated in FIGS. 6 and 7. These depolarizations are quite rapid and point-specific in the receptor field as found in A-delta nerve fibers 50. A-delta nerve fibers propagate toward the spinal cord at 5 to 25 meters/second.

Figure 8:
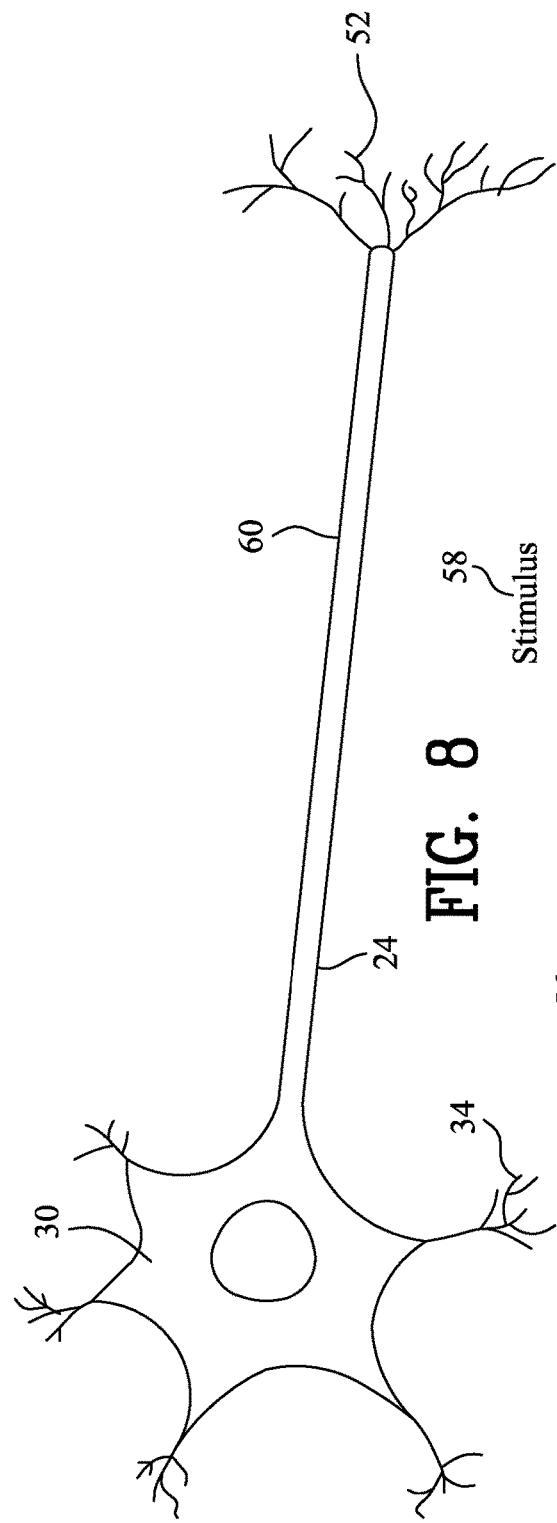
FIG. 8 is a view similar to FIG. 3 illustrating a unmyelinated neuron (C-fiber)
Figure 9:
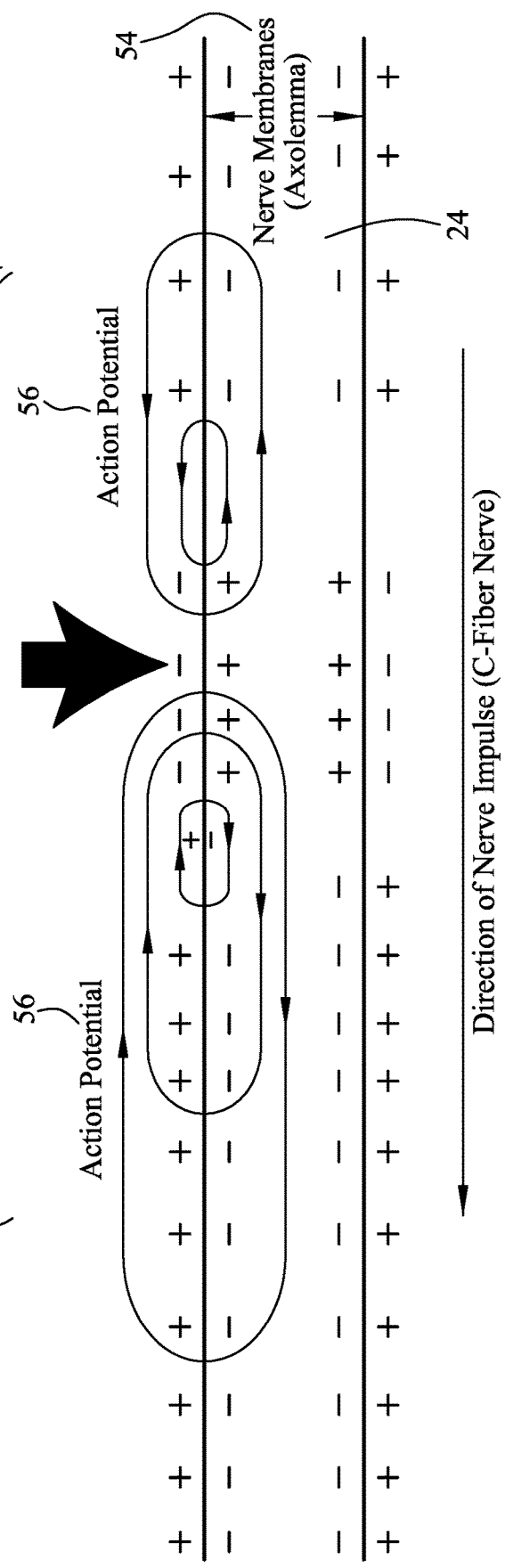
FIG. 9 is an enlarged portion of FIG. 8.

Alternately, nerve impulse may propagate down unmyelinated axons as are found in type A-delta diffuse pain nerve fibers, illustrated in FIGS. 6 and 7 and in type C diffuse pain nerve fibers, illustrated in FIGS. 8 and 9. Here a stimulus causes a nerve impulse propagation in both directions, but the direction toward the spinal cord propagates and continues more readily. Impulse propagation in C-fibers 60 is considerably slower than A-delta fibers at only 0.1 to 2.0 meters/second in those C-fibers 60 conducting pain impulses.

Local anesthetics produce numbness and pain relief by interrupting the nerve's electrical sodium/potassium action potential as it sequentially conducts a nerve impulse, either at the nodes of Ranvier in A-delta sharp pain fibers (FIGS. 6 and 7), or along the unmyelinated C-diffuse pain fibers (FIGS. 8 and 9). Interruption of this action potential, at three sequential nodes of Ranvier in A-delta fiber or equivalent axonal surface of a C-fiber, is enough to block the nerve impulse as it attempts to travel down the nerve's axon to the spinal cord. In this manner, local anesthetics may block both sensory and motor impulses in both A-delta and C-fibers, either as a central (spinal or epidural) or peripheral nerve blocks.

Degree of motor versus sensory block is highly variable with different local anesthetics. While some local anesthetics demonstrate an equal potency for motor and sensory block (such as etidocaine), others show a much greater propensity for sensory blockade over motor blockade (such as bupivacaine). In terms of long-lasting local anesthetic blocks for the prevention of post-operative pain, the amide longer-acting local anesthetics (bupivacaine, ropivacaine, and derivatives) are far superior as these maximize the period of pain relief while minimizing motor blockade. Such long-lasting nerve blocks greatly reduce or even completely eliminate the need for opioid pain medication after surgery if they can be made to last long enough. To this end, bupivacaine and ropivacaine have proven the most efficacious local anesthetics currently available.

In the past, other intellectual property has explored the extension of sensory neural blockade with extensions of analgesia to 72 hours achieved by injection of physiologic bases during or after surgery over a prior injection of a local anesthetic nerve block. However, this previous intellectual property, while extremely broad in its claims, lacks the precision and understanding of the intraneural mechanisms that result in extension of the analgesic period to 120 hour or more. Specifically, Abrahmsohn rejects the simultaneous combination of local anesthetic with sodium bicarbonate ($NaHCO_3$) or sodium carbonate ($Na_2CO_3$), a step essential to this present invention.

The present invention as shown in FIGS. 10-24, includes a long-lasting local anesthetic 99 requiring the combination of the physiologic base 78 with a shorter-acting amide local anesthetic 76 as it 'opens the door' to the penetration of $NaHCO_3$—$Na_2CO_3$ along with a first local anesthetic through the axolemma (axon nerve membrane) into the body of the axon. It is this resulting penetration of $NaHCO_3$/$Na_2CO_3$ into the axon itself, when subsequently combined with subsequent amide long-acting local anesthetic (ALALA-bupivacaine, levo-bupivacaine, ropivacaine) that results in the intra-axonal and extraaxonal precipitation and crystallization of an ALALA-carbonate compound 82. It is this ALALA carbonate precipitate and crystallization 82 that is the cause of 120-hour or longer analgesia. As Abrahmsohn specifically prohibits this direct mixing of NaHCO % and ALALA drugs, the present invention including ALALA-carbonate precipitation and crystallization in vivo is in direct opposition to Abrahmsohn's intellectual property. It is only by forming this precipitate and crystallization in and on the target nerve that a 120-hour block can be achieved.

Mechanism of Formation of the ALALA-Carbonate Precipitate and Crystals

Figure 10:
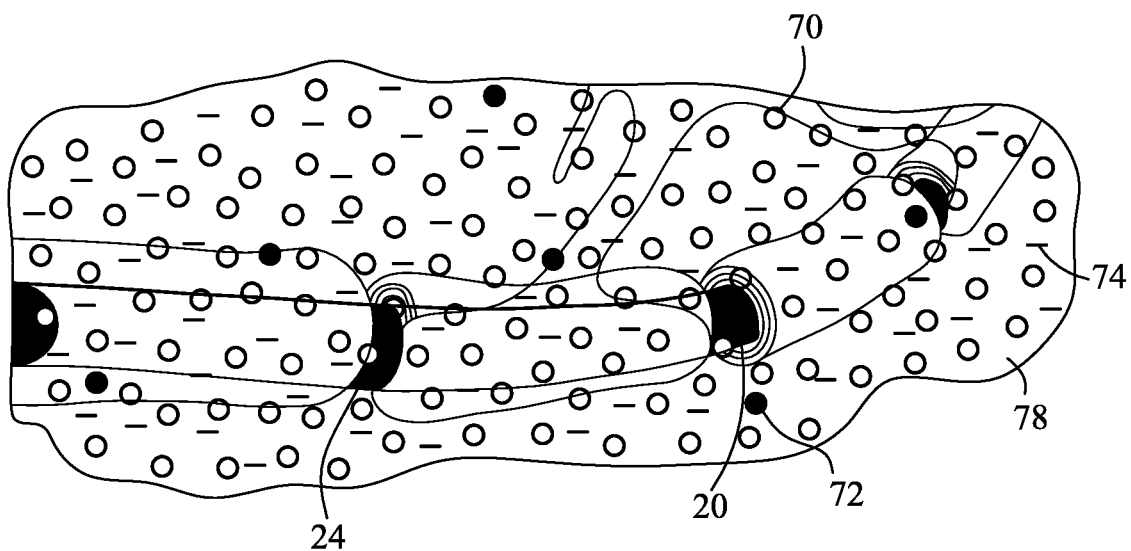
FIG. 10 is a view similar to FIG. 4 illustrating injectate of lidocaine and $NaHCO_3/Na_2CO_3$ (plus possible adjuvants)
Figure 11:
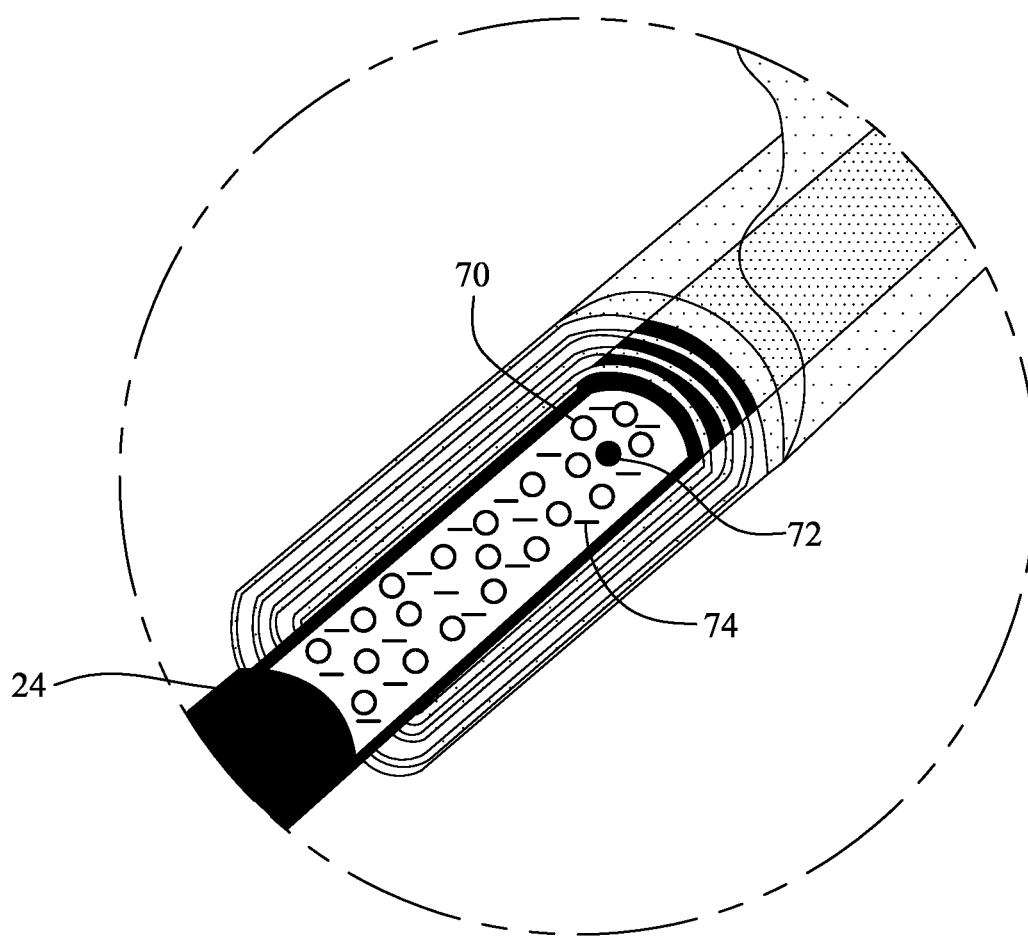
FIG. 11 is a sectional view of FIG. 10.

As shown in FIGS. 10 and 11, the first step of this novel long acting local anesthetic is the injection of a shorter-acting ALA drug that does not precipitate in alkaline solutions of pH 10 or less, such as lidocaine 76, with sodium bicarbonate ($NaHCO_3$)/sodium carbonate ($Na_2CO_3$)/sodium hydroxide (NaOH) mixture, and is in direct opposition to the simultaneous use of local anesthetics and sodium carbonate/bicarbonate bases in prior art (Abrahmsohn). The addition of alkaline $NaHCO_3$/$Na_2CO_3$/NaOH mixture to lidocaine raises the pH of lidocaine and its protonated (+) 72: unprotonated(−) balance shifts predominantly (~95%) to unprotonated (−) molecules 70. This unprotonated form 70 of lidocaine 76 will more readily penetrate the nerve membrane (axolemma) 54 into the axon 24, though, being uncharged, it will not cause nerve impulse blockade (pain relief and numbing). Because of its small size, $NaHCO_3$ and $Na_2CO_3$ move concurrently into the axon 24 readily with unprotonated lidocaine (−) 70, creating a temporary alkaline intra-axonal environment. Some of the unionized lidocaine(−) within the neuron will then begin to equilibrate to form the neurologically active ionized lidocaine (+) responsible for blocking nerve impulses through the neuron. This protonated lidocaine (+) 72 interferes with the nerve's sodium-potassium pump and inactivates it, thus causing the blockade of nerve impulse transmission down the nerve, and a nerve block forms (numbing). With three (3) nodes of Ranvier thus blocked, no nerve impulse can pass down the axon, resulting in the nerve being actively blocked by the local anesthetic.

Figure 12:
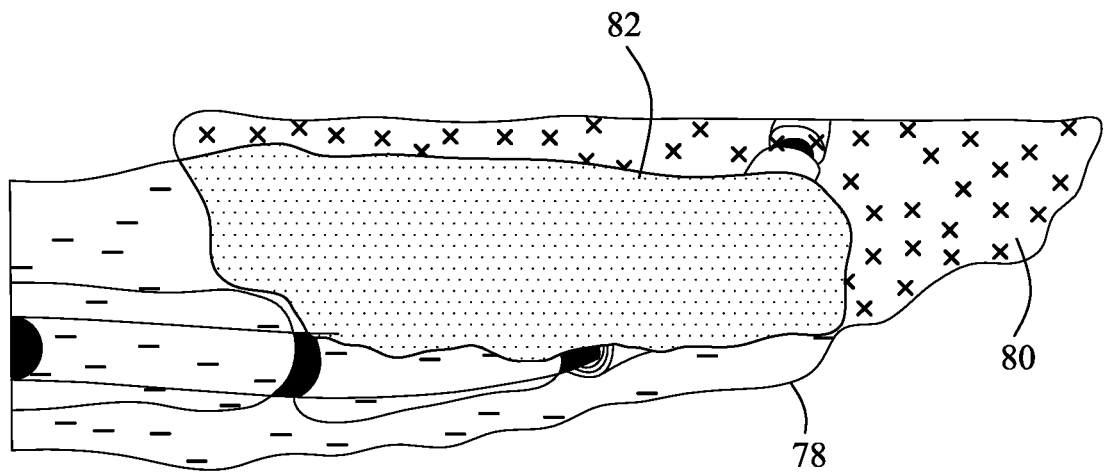
FIG. 12 is a view similar to FIG. 10 illustrating bupivacaine carbonate precipitate.
Figure 13:
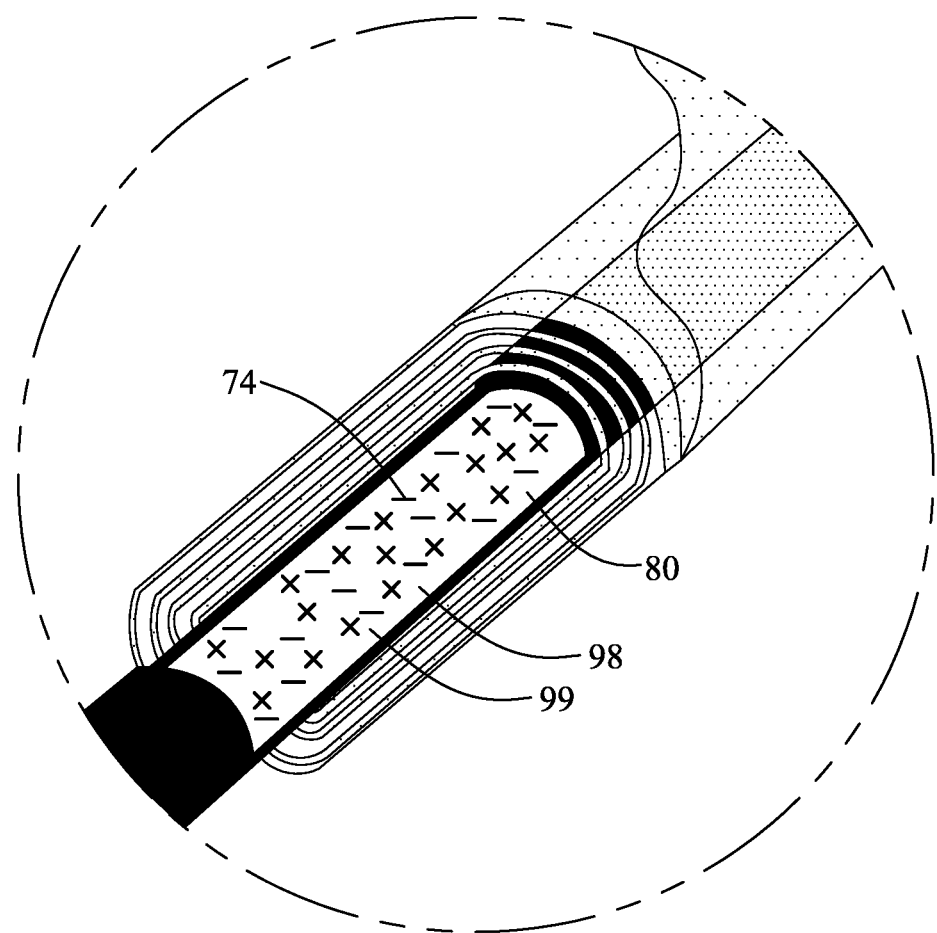
FIG. 13 is a sectional view of FIG. 12.
Figure 14:
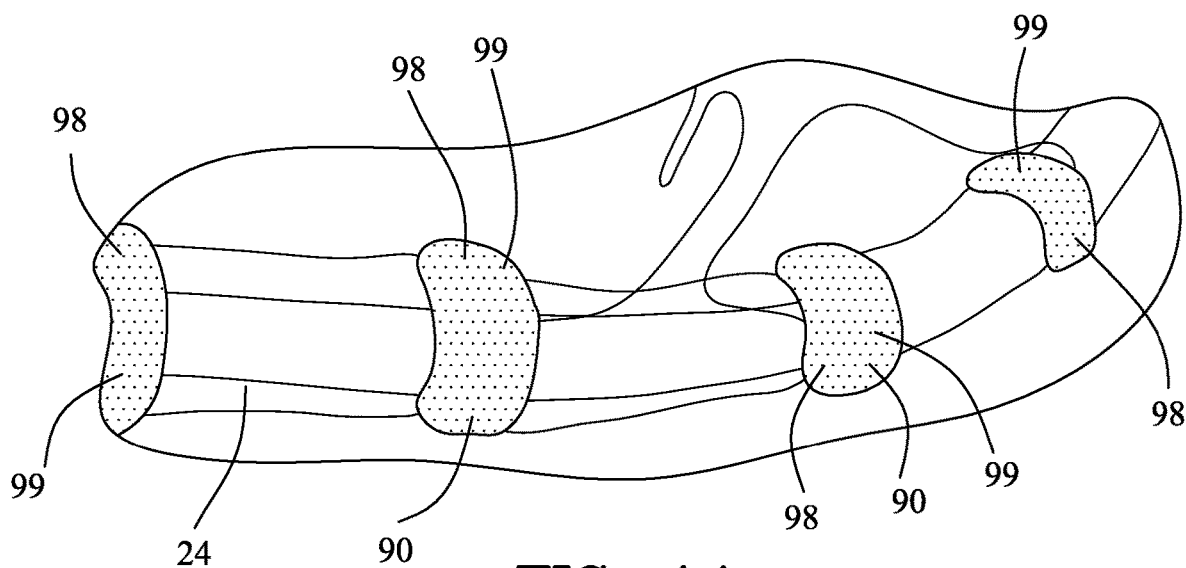
FIG. 14 is a view similar to FIG. 12 illustrating the nodes of Ranvier with extra-axonal deposits of bupivacaine carbonate precipitate crystallizing.
Figure 15:
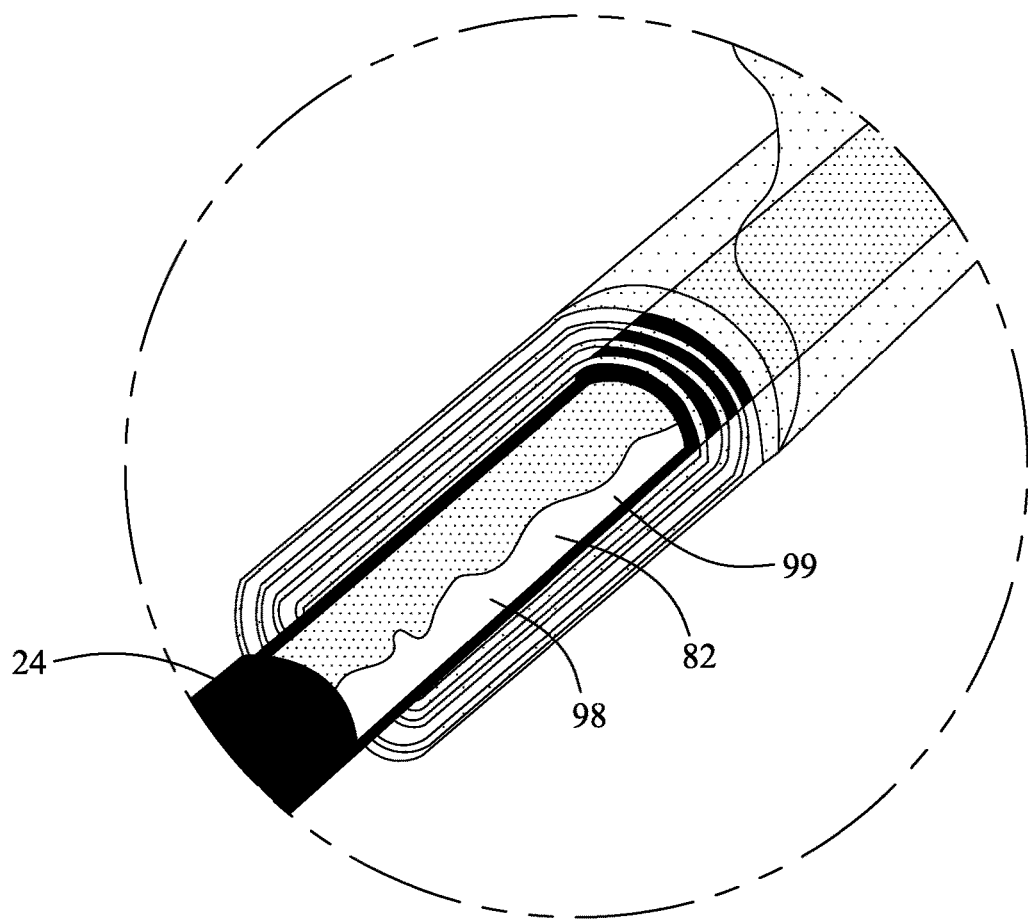
FIG. 15 is a sectional view of FIG. 14.
Figure 16:
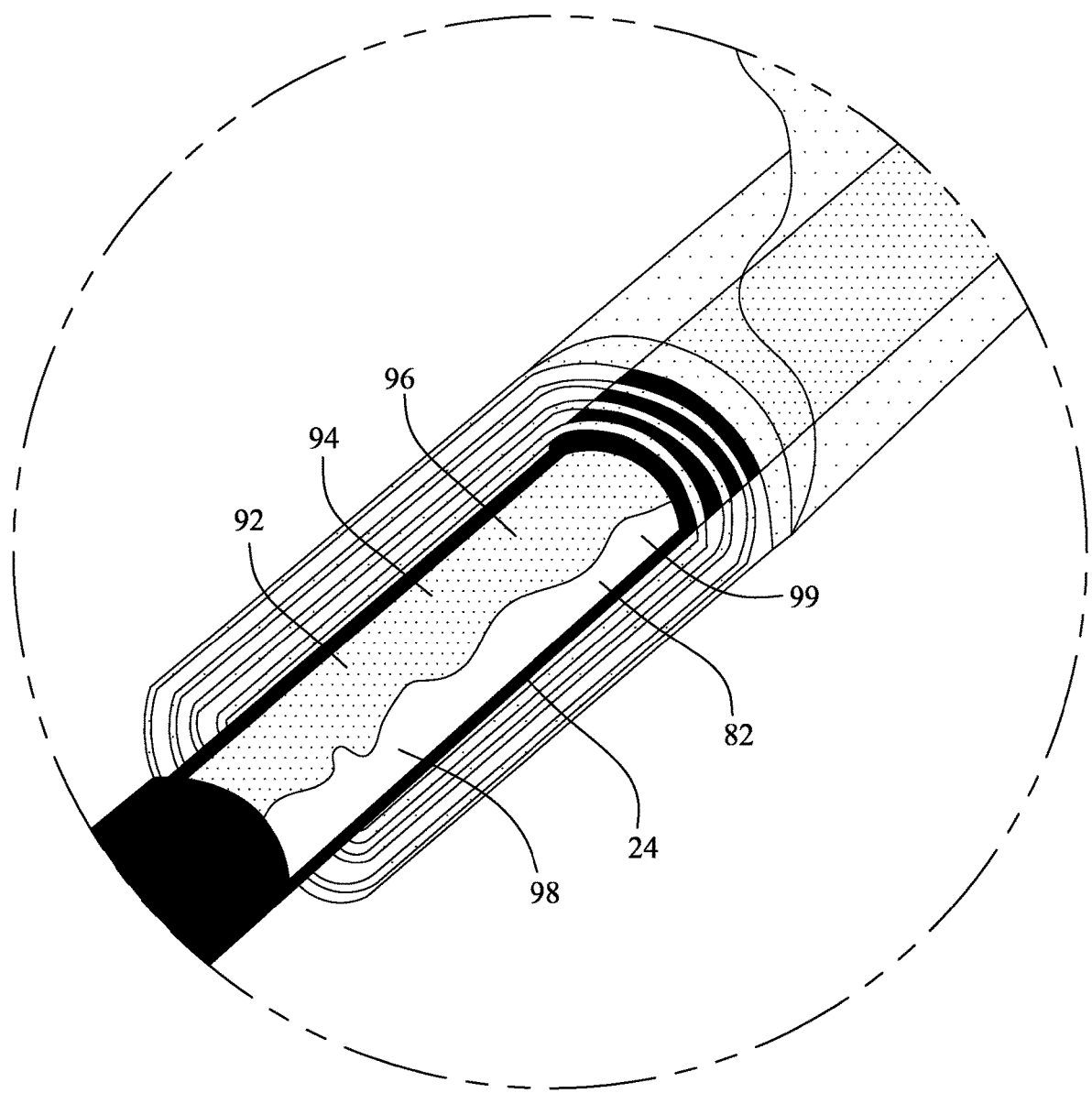
FIG. 16 is an enlarged view of FIG. 15.
Figure 17:
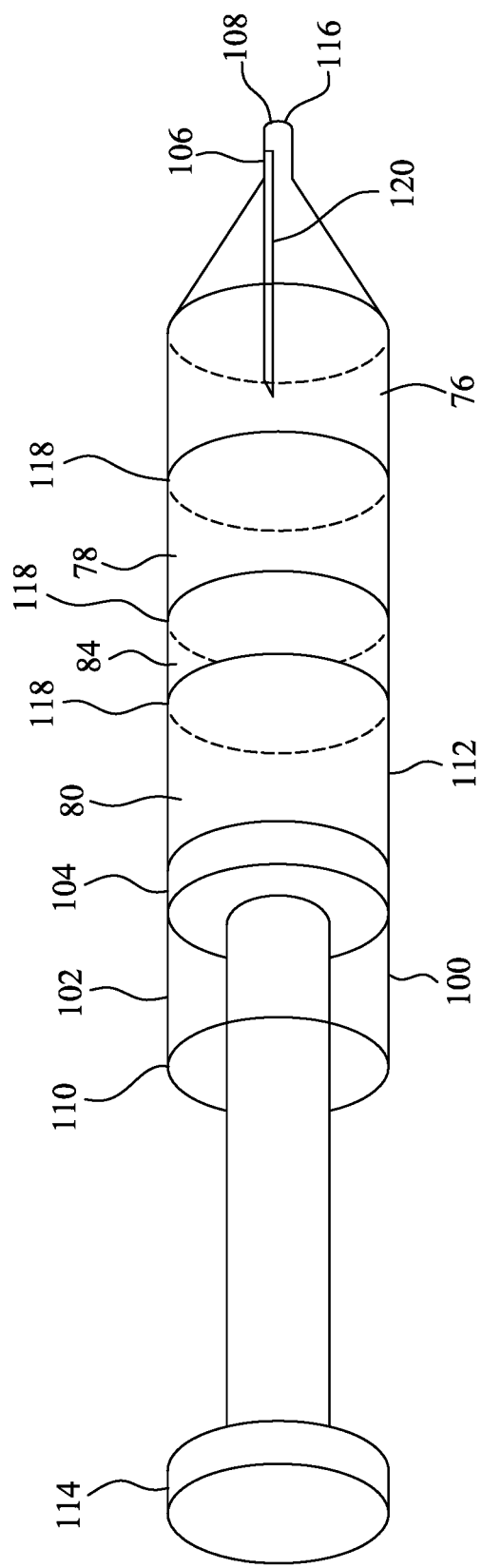
FIG. 17 is a side view of a first embodiment of a dispenser for dispensing the anesthetic nerve block solution.

As shown in FIGS. 12 and 13, once $NaHCO_3$/$Na_2CO_3$ is substantially inside the axon 24 (which occurs within seconds of injection over the nerve), a second injection is made of an amide long-acting local anesthetic 80 such as bupivacaine (shown in FIGS. 12 and 13 as an example of ALALA compounds). Because of their elevated pKa's, ALALA drugs will form a crystalline precipitate 82 in an alkaline environment, both intra-axonally and extra-axonally (at the nodes of Ranvier 20 in A-delta fibers and generally around the axon in C-fibers). When mixed in equal proportions with 8.4% $NaHCO_3$, 0.75% bupivacaine solution (225 mg bupivacaine) will precipitate 92.53% of the bupivacaine drug mass (only 7.47% remains in solution). Similarly, equal volumes of 8.4% $NaHCO_3$ and 0.75% ropivacaine results in 96.50% of the drug mass in precipitated ropivacaine with only 3.50% remaining in solution. It is anticipated levo-bupivacaine will react similarly to levo-ropivacaine at 96.5% conversion to precipitate and crystallization when this drug becomes available.

As shown in FIGS. 12-16, the crystalline ALALA-carbonate precipitate 82 (bupivacaine carbonate shown in FIGS. 12-16) will collect and crystalize in and around the nerve's axon 24 in both A-delta and C-fibers 90. Together, these alkaline ALALA-precipitates (at pH's>7.4) condensing into larger crystals to form an inactive depot of local anesthetic 90 which only slowly degrades into its unionized form (ALALA−)+$H_2O$ &$CO_2$ 96 before re-equilibrating into the ionized form (ALALA+) that continues the nerve blockade and its resultant pain relief for multiple days. Thus it is the alkaline pH of the ALALA-carbonate precipitate crystals that are responsible for the extended nerve block lasting days.

The in-vivo formation of a crystalline bupivacaine carbonate collects as a precipitate deposit within and outside the axon (at the nodes of Ranvier in A-delta fibers and along the whole axon in C-fibers). While much of the extra-axonal bupivacaine carbonate is eventually swept away by circulating lymph, a significant percentage remains to act as a bupivacaine depot contributing to the extended duration of the nerve block. Most of the extension of nerve block duration is due to the quantity of bupivacaine carbonate precipitate formed within the axon in both A-delta and C-fiber neurons.

ALALA-carbonate precipitating within the body will not remain stable, but will rather break down to the unprotonated (−) form plus carbon dioxide ($CO_2$), water ($H_2O$), and salt (NaCl) as the alkaline environment within the axon returns toward normal pH 7.4. $CO_2$, $H_2O$, and NaCl reabsorb into the lymph and blood wherein $H_2O$ and NaCl are eventually eliminated through the kidneys and $CO_2$ through the lungs. Because the initial breakdown of bupivacaine carbonate generates unprotonated (−) bupivacaine in an alkaline milieu, protonated (+) bupivacaine generation is limited but is enough to extend the duration of the established nerve blockade. As more of the pH of the alkaline intra-axonal milieu returns toward pH 7.4, more and more of the bupivacaine carbonate gains a proton, becomes active blocking the neuron's sodium-potassium pump, reinforcing the nerve blockade until finally all of the bupivacaine carbonate has broken down to bupivacaine (−), protonated to bupivacaine (+), blocked the nerve receptors, and been metabolized. Only as the last of the bupivacaine (+) is metabolized does the nerve block effect wear off in individual A-delta and C-fibers.

Because nerve metabolism in A-delta fibers is more rapid than C-fibers, the A-delta pain fibers will recover normal sensation more rapidly than their C-pain fiber counterparts. This generally results in an A-delta nerve block lasting 48-72 hours. However, the desirable C-pain fiber block can last 120 hours or more. Sensory nerve blocks of 120 hours can relieve the need for opioid-based analgesics after surgery. It is this elimination of the need for post-operative opioid prescriptions will close the gateway that now exists, the gateway by which many people enter into opioid addiction.

Adjuvants

Other peripheral nerve block adjuvants 89 may be added this ALALA-carbonate block to augment it. These include epinephrine as a vascular marker and vasoconstricting agent, $\alpha^2$-agonists such as clonidine, dexmedetomidine, etc. and steroids such as dexamethasone, betamethasone, triamcinolone etc. Steroids 88 separately can crystallize amide local anesthetics by themselves and augment the crystallization/precipitation also caused by $NaHCO_3$, $Na_2CO_3$, NaOH and other physiologic bases by a separate mechanism.

Recently it has been noted that physiologic bases 76 ($NaHCO_3$/$Na_2CO_3$/NaOH) are not the only compound class capable of precipitating local anesthetics, ALALA compounds in particular. Steroids 88 also have this effect precipitating ALALA compounds. Whether this results in intraneural or extraneural deposition of ALA local anesthetic is not yet clarified. However, it is already known in the literature steroid supplementation of ropivacaine and bupivacaine in ALALA peripheral nerve blocks can extend blocks normally lasting 16-hours to 24-hours and sometimes up to 30 hours. In this invention, inclusion of steroids in the ALALA-compound blocks does extend the resulting analgesia, whether by intraneural (axonal) or extraneural deposition of the ALALA-carbonate compound. However, elimination of $NaHCO_3$ invariably results in blocks of ~30 hours or less.

It is relevant to this invention to note variable combinations of drug masses for $Na_2CO_3$, $NaHCO_3$ and various steroids (currently dexamethasone and betamethasone), can result in titratable time frames for analgesia, depending on how long analgesia after surgery is desired. It is conceivable various combinations of $NaHCO_3$ (pH=8−9) and $Na_2CO_3$ (pH=1:10-11) can create any desired alkaline milieu to control absorption of carbonate base into the axon of neurons as well as that milieu's pH. pH is the control determining the quantity of precipitate and crystal size in the formation of ALALA-carbonates and is further modified by corticosteroids. As we have discovered, even higher concentrations of NaHCO/$Na_2CO_3$ and/or steroids can result in considerably longer periods of analgesia exceeding 120-hours. Thus, creation of predictable and titratable analgesic periods is a function of the drug masses and concentration of constituent components in the ALALA-carbonate nerve block. Thus, a nerve block can be programmed to last for a specific period as a function of the masses/concentrations of each component in that ALALA-compound block.

Protocol for the Creation of the ALALA-Compound Nerve Block

As shown in FIGS. 17-23, the establishment of a 5-day peripheral nerve block involves the injection of two separate and sequential solutions to form the ALALA-compound precipitate and crystals in vivo around the nerves for specific nerve blocks. These solutions form the ALALA-compound precipitates and crystals. As the two solutions must be kept separate until injection over the specific nerve is accomplished, the solutions may then react to form the ALALA-compound precipitate and crystals in vivo.

Figure 20:
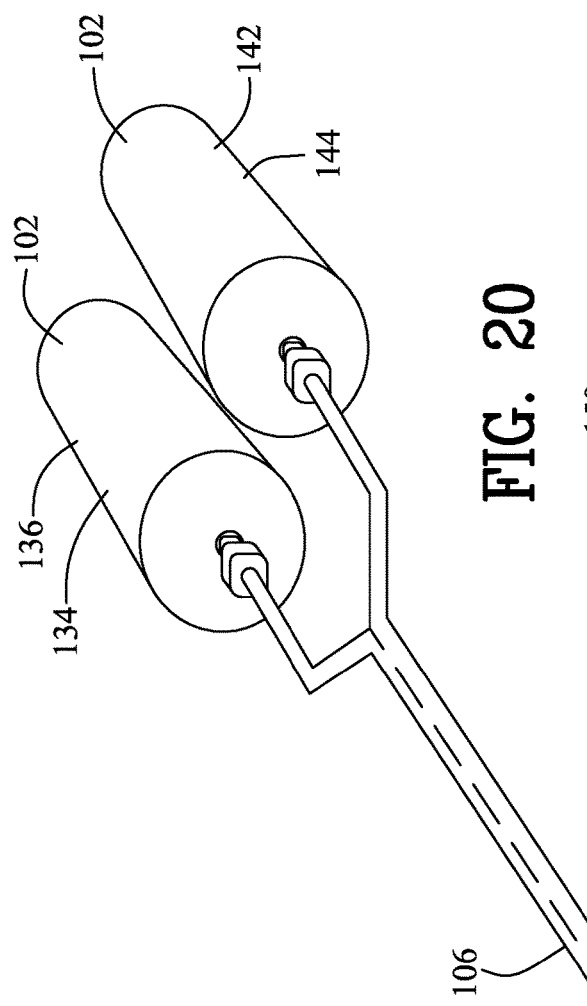
FIG. 20 is a side view of a third embodiment of the dispenser for dispensing the anesthetic nerve block solution.
Figure 21:
FIG. 21 is an enlarged portion of FIG. 20.

This separation of solutions by two different means:
1. The sequential injection of two separate solutions through a single needle (FIGS. 17-19 and 22).
2. The simultaneous injection of both solutions through a bifurcated needle where mixing occurs only at the needle tip(s) opposite the target nerve (FIGS. 20 and 21).

These alkaline solutions are:
1. Solution 1-4% lidocaine+1:200,000 epinephrine+8.4% –10% $NaHCO_3$. Proportions of 4% lidocaine and 8.4% $NaHCO_3$/$Na_2CO_3$ are equal. Epinephrine 86 is present at a concentration of ~3 mcg/ml, primarily as a standard vascular marker producing mild tachycardia if leakage into the vascular system occurs. When Solution 1 is given, a pulse-oximeter or EKG rhythm strip must be run to confirm no tachycardia for 2 minutes to ensure Solution 1 has no leakage into the vascular system with a resulting tachycardia greater than 15% above baseline pulse.

As amide longer-acting local anesthetics can be cardiotoxic and can cause seizures, even cardiac arrest, such a provision to prevent inadvertent injection of Solution 1 into the vascular system is a mandatory requirement. This precaution is critical for patient safety with ALALA-compound blocks.

This use of epinephrine as described in 1. and 2. is the exact protocol currently followed (test dose) in all hospitals since the 1980's to prevent cardiotoxic reactions to ALALA drugs in an epidural catheter after placement and prior to use.

2. Should a tachycardia of 15% or more over baseline pulse occur during the slow injection of Solution 1, the block is immediately aborted as the tachycardia from epinephrine 86 is taken as proof of intravascular leakage of Solution 1. Under such conditions, if Solution 2 is subsequently injected, Local Anesthetic Systemic Toxicity could result with patient seizures and cardiac arrest. For this reason, a standard protocol wait of 2-minutes is given between the injection of epinephrine containing Solution 1 and Solution 2. Solution 2 is injected only if no increase in pulse rate greater than 15% above baseline is determined within 2 minutes.

3. A clearing solution 84 injection through the needle to prevent the mixing of Solution 1 with Solution 2, thereby creating a precipitate/crystals which can clog the lumen of the needle before the full injection of Solution 2 can be accomplished. This would prevent the complete mixing of Solutions 1 and 2 and thus incomplete precipitate/crystal formation. Solution 1 must be washed clear from a single-lumen needle before Solution 2 is injected to prevent this.

4. Solution 2-0.75% Bupivacaine, 0.75% levo-bupivacaine, or 1% ropivacaine used as a single component for Solution 2, usually in a volume equal to Solution 1.

If higher concentrations of ALALA compound components are utilized, further prolongation of the analgesic block with greater and larger crystal formation can be achieved. As $NaHCO_3$ is already a saturated solution, attempting to raise the mass of $NaHCO_3$ in the solution and thereby the pH is not possible. But this can be done by increasing the $Na_2CO_3$ concentration in the $NaHCO_3$:$Na_2CO_3$ mixture and thereby raising the pH to provide a higher pH in the final mixture, resulting in greater precipitate and crystal formation.

When physiologic 8.4% NaHCO (at a pH ~8) is added to an equal volume of 4% lidocaine in Solution 1, the final concentration of $NaHCO_3$ and lidocaine are cut to 4.2% and 2% respectively, and the pH drops. This is further diluted when an equal volume of Solution 2 is added to this mixture perineural to form the precipitate with only 2.1% $NaHCO_3$. This dilution lowers the acid:base balance of the final solution to a point only marginally above pH 7.4 (physiologic).

If the pH of the $NaHCO_1$ of Solution 1 is elevated by adding $Na_2CO_3$ to a point where the pH of the final perineural solution is ~pH=8, far greater concentrations of ALALA-carbonate precipitate can be formed, resulting in longer to much longer, periods of analgesia from the nerve block. This can prove very useful in larger and more complex surgeries, and even chronic pain syndromes.

As the pH of the physiologic bases in Solution 1 are raised to prolong analgesia, the same can happen by raising the drug mass of ALALA drugs, steroids, $\alpha^2$-agonists such as clonidine and dexmedetomidine, NSAID, or NMDA agonists with any other adjuvants to increase the axonal content of these drugs in the precipitate/crystals. These can functionally extend the analgesia obtained to 14 days or more, helping to suppress the neural feedback causing Chronic Regional Pain Syndromes (CRPS) and allowing the spinal cord to reset itself toward normal. Further animal experimentation will prove which drugs in what concentration are more useful to this end than our current mixture of Solutions 1 and 2.

When these solutions are used for sequential injections through a single needle (FIGS. 17 and 22), the materials of Solution 1 must be cleared from the needle before Solution 2 can be injected. The $NaHCO_3$ in Solution 1 can cause the bupivacaine or ropivacaine of Solution 2 to precipitate in the needle and clog it. Therefore, Solution 1 must be irrigated clear from a single lumen needle before Solution 2 can be injected through that needle. This problem is obviated by the present invention for a delivery device or dispenser, co-joined or internally bifurcated needles, capable of injecting these solutions sequentially while invariably eliminating the possibility of a clogged needle due to precipitate (FIGS. 18-21).

Once Solution 1 is injected around the peripheral nerve, the $NaHCO_3$ and $Na_2CO_3$ will push the protonated/unbound physiochemical balance of lidocaine toward the unbound portion at approximate 95%. As the unbound fraction of a local anesthetic is critical to its tissue penetration of the axon. Lidocaine will then be taken into the axon in greater mass than usual, and with this greater mass of lidocaine, $NaHCO_3$ is also taken into the axon.

$NaHCO_3$ in Solution 1, when mixed with bupivacaine, levo-bupivacaine, or ropivacaine of Solution 2, will cause these drugs to immediately precipitate into crystals in this alkaline solution. When mixed in equal proportions with 8.4% $NaHCO_3$, 0.75% bupivacaine solution (225 mg bupivacaine) will precipitate 93.53% of the bupivacaine drug mass (only 7.47% remains in solution). Similarly, equal volumes of 8.4% $NaHCO_3$ and 0.75% ropivacaine results in 96.50% of the drug mass in precipitated ropivacaine with only 3.50% remaining in solution.

Without moving an ultrasound-placed single-lumen injection needle from its position next to the nerve, that needle is cleared of $NaHCO_3$ (using saline or air), before Solution 2 is injected in a volume equal to that of Solution 1 by sequential injection. Note this step is unnecessary with co-joined or internally bifurcated needles.

As bupivacaine (or ropivacaine) flows into the $NaHCO_3$/lidocaine Solution 1 around the nerve, the bupivacaine begins to precipitate. The predominance of the drug will precipitate outside the axolemma and so will be removed by usual lymph flow around the nerve over time. Steroids have been noted to precipitate local anesthetics in vitro and are expected to accomplish this same function in vivo. A recent paper has noted this reaction as a precaution against the combination of steroids and bupivacaine in epidural anesthetics. However, what would be bad for epidural blocks can accomplish much longer blockade when used for peripheral nerve analgesia in lieu of opioids. Betamethasone and dexamethasone can create greater precipitation with bupivacaine and ropivacaine and result in even longer long-acting local anesthetic blocks when incorporated with $NaHCO_3$ in Solution 1.

The variable drug masses of $NaHCO_3/Na_2CO_3/NaOH$ and other steroids create variable lengths of effective analgesia, depending on the concentrations/drug masses of $NaHCO_3$ and steroids used in Solution 1. Theoretically other steroids, not listed here, may yet prove even greater intraaxonal or nodal precipitation of amide long-acting local anesthetics with proportionally greater analgesic time after surgery.

Only approximately 11.9% of bupivacaine penetrates the axolemma or node before it precipitates as bupivacaine carbonate. It is this small amount of bupivacaine within the axolemma/node that results, primarily, in continuing neural blockade for periods of 120 hours or more.

But by altering the final pH of the combination of ALALA drugs with all adjuvants and bases/precipitates, these solutions can be forced to create much more of the ALALA precipitate/crystals for longer and denser nerve blocks. This is the goal of the Alternate Protocol for the Creation of the ALALA-Precipitate Nerve Blocks.

Alternate Protocol for the Creation of the ALALA-Preciopitate Nerve Block

As shown in FIG. 24, an alternate protocol exists which shows advantages over the original protocol when placing a nerve block desired to last more than 120 hours.

In this alternate protocol, it is first necessary only to prove block needle placement has not opened a connection to the vascular system with a 'test-dose' with or without adjuvants as shown in Stage 1 of FIG. 24. However, if there is connection to the vascular system revealed by a tachycardia≥115% of baseline as a result of this test dose, the local anesthetic (lidocaine), with epinephrine plus any included adjuvants, will be all the nerve block the patient will received at that location and at that time. The ALALA drugs will not be given nor will the physiologic base(s). In this manner, intravascular injection of ALALA drugs with risk of seizure, cardiac arrhythmias and arrest, will be avoided.

There is still the Mandatory 2-Minute Wait (shown in Stage 2) as the test dose revealing whether or not there is connection to the vascular system of the body. Again, in this manner, ALALA drugs causing cardiotoxic reactions, including seizure, arrhythmias, and cardiac-arrest, are avoided by use of the test dose. This has been done with obstetric epidural catheters since the 1980's to prevent ALALA cardiotoxic reactions.

Immediately after Stage 2 is Stage 3 with the injection of the ALALA drug(s) in a drug mass necessary to produce the desired duration of analgesia from this nerve block. This stage may contain adjuvants, but not the precipitating steroids nor physiologic bases which would cause precipitation in the ALALA drug mass when combined outside the body and target nerve(s).

In Stage 4, with the ALALA drug already deposited perineurally, the single-lumen needle is flushed with a clearing solution, such as saline. This sets up the block needle for Stage 5 and the injection of the physiologic base(s) and/or precipitating steroids.

In Stage 5, the calculated base(s) and steroid(s) are injected to raise the pH of all injected drugs in Stages 1-4 to a pH of ~8.0 (7.4 to 8.4) so as to form the correct amount of precipitate and crystals (physiologic base and steroid) to result in peripheral nerve block of the desired duration from 3 to more than 30 days.

As this alternate method is pH driven to a final in vivo pH, volumes of injectates no longer must be equal. Much smaller doses of higher pH bases/steroids may be used to produce the final pH desired in the mixture of ALALA drugs and adjuvants to produce the desired precipitates for the duration of analgesia desired.

By optimizing pH in the nerve block by this alternate method, the amount of precipitate (physiologic base(s) and steroid-induced) can be controlled, thereby controlling block density and duration as desired. A simple table will dictate type and mass of each drug, target pH, and duration, even density obtained so as to produce a nerve block of a specific duration and density as desired. This is especially necessary when treating chronic pain patients, especially those with Chronic Regional Pain Syndrome.

Multiple academic papers advise against the addition of too much-carbonate base and steroids (especially corticosteroids) as the cause of ALALA drug (bupivacaine, levo-bupivacaine, ropivacaine) precipitation. Tetracaine, an Ester Long-Acting Local Anesthetic (ELALA), with a pKA higher than bupivacaine, will also precipitate in-carbonate bases and steroids.

Though academic publications recommend limits to avoid forming local anesthetic precipitates, our intellectual property intends to form these precipitates within the nerve cell and axon as depots of ALALA or ELALA drugs that continue the nerve block well beyond 3 days. Drug mass and composition of these precipitates determine the duration of the nerve block so created and therefore the duration of pain relief.

Formation of ALALA-precipitates within the nerve is the basis for longer-term interruptions of the sodium-potassium ion pump within the neuron. When this pump is disabled, so is neural transmission of pain impulses and thereby analgesia is obtained for the post-surgical and posttrauma patient when a nerve block is administered.

Various-carbonate and steroid drugs exist, when combined with ALALA (and ELALA) drugs to form local anesthetic precipitates of varying longevity from 3 to 30 days or more.

Physiologic carbonate bases are primarily composed of sodium bicarbonate ($NaHCO_3$), sodium carbonate ($Na_2CO_3$), and sodium hydroxide (NaOH). Each of these solutions has a different saturation pH, and so various combinations of these solutions can create a final common solution at a desired pH. This is critical in obtaining the desired amount of ALALA or ELALA precipitate intra-neurally when a specific analgesic period is desired from a peripheral nerve block.

As discovered in our laboratory, 8.4% $NaHCO_3$, when combined in vitro with bupivacaine or ropivacaine, results in precipitates of 93.5% and 96.5% respectively of the parent ALALA drug. But when $NaHCO_3$ is further diluted with lidocaine and adjuvants, then later again diluted with an equal volume of the ALALA drug, the percentage of $NaHCO_3$ is diluted from 8.4% to 2.1% with a concomitant drop in pH and a much lower conversion of the ALALA drug to precipitate. Controlling the pH of the final combination of all these drugs and bases more efficiently controls the percentage of ALALA converted to precipitate and crystals and thereby the duration of the resulting nerve block.

Similarly, combination of ALALA (or ELALA) local anesthetics with steroids, especially corticosteroids, also causes ALALA-precipitates. Some of these precipitates migrate into the neural axon to form intra-neural ALALA or ELALA steroid precipitates. Cortcosteroids known to be useful in forming these precipitates include dexamethasone, betamethasone, and triamcinolone. Such combination of steroids with ALALA or ELALA drugs can result in clinically useful precipitates generally indicated by the table below.

General Table 1 of Possible Local Anesthetic and Precipitating Bases and Steroids

|  | Sodium Bicarbonate $NaHCO_3$ | Sodium Carbonate $Na_2CO_3$ | Sodium Hydroxide NaOH | Dexa-Methasone | Beta-Methasone | Triamcinolone |
|---|---|---|---|---|---|---|
| Bupivacaine | Bupivacaine Carbonate (lower pH) | Bupivacaine Carbonate (higher pH) | Bupivacaine Carbonate (highest pH) | Bupivaciane Dexa-Methasone Precipitate | Bupivacaine Beta-Methason Precipitate | Bupivacaine Triamcinolone Precipitate |
| Levo-Bupivacaine | Levo-Bupivacaine Carbonate (lower pH) | Levo-Bupivacaine Carbonate (higher pH) | Levo-Bupivacaine Carbonate (highest pH) | Levo-Bupivaciane Dexa-Methasone Precipitate | Levo-Bupivacaine Beta-Methason Precipitate | Levo-Bupivacaine Triamcinolone Precipitate |
| Ropivacaine | Ropivacaine Carbonate (lower pH) | Ropivacaine Carbonate (higher pH) | Ropivacaine Carbonate (highest pH) | Ropivaciane Dexa-Methasone Precipitate | Ropivacaine Beta-Methason Precipitate | Ropivacaine Triamcinolone Precipitate |
| Tetracaine | Tetracaine Carbonate (lower pH) | Tetracaine Carbonate (higher pH-) | Tetracaine Carbonate (highest pH) | Tetracaine Dexa-Methasone Precipitate | Tetracaine Beta-Methason Precipitate | Tetracaine Triamcinolone Precipitate |

General Table 2 of Possible Local Anesthetic and Precipitating Bases and Steroids

| Bupivacaine± | Physiologic Base(s)± | Precipitating steroids± | Adjuvants± | Other drugs and/or adjuvants? |
|---|---|---|---|---|
|  | $NaHCO_3$ @0-100% of base (=100) plus | Dexamethasone at 0-100% of steroid | Dexmedetomidine @0-1000 mcg |  |
|  | $Na_2CO_3$ @0-100% of base (=100) plus | Betamethasone at 0-100% of steroid | Clonidine @0-500 mcg |  |
|  | $Na_2CO_3$ @0-100% of base (=100) plus | Triamcinolone at 0-100% of steroid | NSAIDS. Such as a ketorolac derivative 100 mg NMDA-antagonists such as ketamine or dextromethorophan in 0-100 mcg and 0-100 mg respectively μ-2 opioids such as Fentanyl 0-1000 mcg Meperidine 0-200 mg and morphine 0-50 mg |  |

-continued

General Table 2 of Possible Local Anesthetic and Precipitating Bases and Steroids

| Bupivacaine± | Physiologic Base(s)± | Precipitating steroids± | Adjuvants± | Other drugs and/or adjuvants? |
|---|---|---|---|---|
| | 100 NaHCO$_3$ × 100 Na$_2$CO$_3$ × 100 NaOH = 1,000,000 possible combination of NaHCO$_3$, Na$_2$CO$_3$, and NaOH with bupivacaine alone. This is further multiplied by | Again you wind up with approximately 1,000,000 variation of the precipitating steroids to pit against the 1 million variations of the physiologic bases, resulting in at least 1 × 10$^{12}$ possible useful combinations with bupivacaine | This offers the possibility of 2.5 × 10$^{16}$ possible variations. This makes the total variations in this block for bupivacaine = 1 × 10$^{28}$ combinations for bupivacaine alone. | More |

As shown in General Table 2 above, once Levo-bupivacaine and ropivacaine are taken into account, die total variations conceivable are 3×10$^{28}$. It is possible some of these chemical interactions could eliminate PABA from the breakdown of tetracycline. In this case, the total conceivable useful variations from this matrix is 4×10$^{28}$.

General Table 3 Currently Identified ALALA-Precipitate Blocks

| Bupivacaine± | Physiologic Base(s)± | Precipitating Steroids± | Adjuvants+ | Lidocaine + epinephrine |
|---|---|---|---|---|
| | NaHCO$_3$- 75%-100% | Dexamethasone- 1 mg to 10 mg | Dexmedetomine- 10 mcg- 1000 mcg | |
| | Na$_2$CO$_3$ 25%-0% | Betamethasone- 1 mg to 20 mg | Clonidine- 30 mcg to 300 mcg | |

Table 3 above illustrates the currently identified components of the ALALA-precipitate blocks:

1. The ALALA drugs-bupivacaine, levobupivacaine, ropivacaine.

2. The physiologic bases-NaHCO$_3$ at pH~8.0-8.2—the usual primary physiologic base, and Na$_2$CO$_3$ at a saturated solution pH of ~8-9, but crystals added directly to a mixture are at a pH=11.5.

The subject invention anticipates both of these bases will be added together to solutions in order to control pH and thereby precipitate ALALA compounds in the range of the final mixture to be found between pH 7.5 and pH 8.4. Adequate alkaline pH is necessary to control degree of ALALA precipitation that controls the duration of these ALALA-precipitate nerve blocks. If a smaller total volume is required for the final volume of injectate, even a few crystals of NaOH could be added to the NaHCO$_3$/Na$_2$CO$_3$ solution to bring them to the desired pH just prior to the nerve block injection(s). It is the intention of the subject invention that concentrations of NaHCO$_3$ go up as Na$_2$CO$_3$ go down, accounting only for a 25-fold changes in physiologic base.

3. The Precipitating Steroids, primarily corticosteroids Dexamethasone and Betamethasone. These two corticosteroids are currently used in regular peripheral nerve blocks to extend ALALA blocks from 12-16 hours to an effective range of up to 24-hours before wearing off. Given Hwang's cautionary paper, the likely cause is ALALA-precipitates filling in the time gap between the initial lidocaine+epinephrine wearing off and the ALALA-carbonates reverting back to protonated ALALA continuing the nerve block lidocaine began. Useful dosage ranges for these corticosteroids are as given above. One or both corticosteroids may need to be used simultaneously, resulting in both 10× and 20× changes in the steroid use.

4. The Adjuvants-these are primarily the $\alpha^2$-agonist drugs-dexmedetomidine and clonidine, agents known to block $\alpha^2$-pain receptors in the spinal cord and believed to also function in peripheral nerves. Certainly dexmedetomidine and clonidine, along with the corticosteroids, have been noted to extend standard peripheral nerve blocks with bupivacaine and ropivacaine ~50%. Increased dosage of these $\alpha^2$-agonist drugs results in increased duration of these nerve blocks. These drugs are each used in 100× variations.

Therefore the conceivable variations of these blocks for bupivacaine are 25×10×20×100×100=5,000,000 variations of these drugs with bupivacaine. Same bupivacaine and ropivacaine for a sum total of 15,000,000 variations of workable compounds with these ALALA drugs.

Tetracaine, though it will precipitate in physiologic base and corticosteroids, is not considered as it releases toxic PABA in the breakdown of these large peripheral nerve block drug masses. This is too dangerous for use in humans until a safer variation of ELALA drugs are found or a means to detoxify them.

While other variations may show some promise, these are the variations most likely to create the long-lasting blocks of 120-hours or more sought by the present invention.

Both ALALA-carbonate and steroids precipitates can form intra-neural precipitate depots which, upon degradation form salt, water, carbon dioxide and the unprotonated (−) ALALA drug. The unprotonated ALALA form will gain a proton and equilibrate with its protonated (+) and neutrally active form. It is this neutrally active protonated form of the ALALA drug that blocks the sodium-potassium ion pump in the neuron and axon, thus stopping painful nerve transmission and results in both numbness and analgesia.

The potential combinations of these drugs and bases comprise an elemental matrix of total 3×10$^{28}$ different combinations that can produce these analgesic precipitates. This initial matrix must then be multiplied by the number of different adjuvants including all the $\alpha^2$-adjuvants, NSAIDS, NMDA-antagonists, and even $\mu^2$-agonists for those blocks that include these. Multiply all these variations by the various percentages of each-carbonate base and drug masses of each of the various steroids that can affect density and longevity of the final nerve block. This would result in a matrix of thousands to even tens-of-thousands of entries and variations to control nerve block density and longevity.

Titration of carbonates or steroids to a specific target pH in the final ALALA compound will control density and longevity of the nerve block; thus various dilutions of-carbonate bases and steroids can produce the desired final pH and precipitates as needed for the intended nerve block density and longevity.

Given, some of these combinations would not produce acceptable analgesia and even others would not be practical for use in biological tissue. But most would have some efficacy to produce ALALA (or ELALA) precipitates resulting in various nerve blocks with analgesia between 3 and 30 days or more. Other compounds may be found in the future to augment these same intra-neural ALALA (or ELALA) precipitates and so produce more efficient and titratable nerve blocks and analgesia. These combinations may be used with peripheral nerve block or field blocks to produce the post-surgical and post-trauma analgesia for the specific block density and duration as desired.

Ester Local Anesthetics

It is hereby noted tetracaine, an ester local anesthetic, has a pKa even higher than bupivacaine and will precipitate in the presence of $NaHCO_3$ and $Na_2CO_3$ and could also produce a long-acting local anesthetic block as well. However, as an ester local anesthetic, tetracaine will break down to para-amino benzoic acid (PABA), a known allergen capable of precipitating severe, even fatal, allergic reactions. Given these anaphylactic reactions are known in doses of 10 mg and less, the 100 mg to more than 200 mg doses required for peripheral nerve blocks would have a greatly increased frequency of occurrence. It is even likely a 200 mg dose would uniformly be fatal in humans. For this reason, until laboratory testing can produce an ester or other long-acting local anesthetic action greater than that of bupivacaine without notable toxicity, tetracaine will not be utilized in volume-dependent peripheral nerve blocks, as are currently common. However, tetracaine's inclusion in this intellectual property is necessary and will be utilized and claimed if and when a nonallergenic variant of this block without prohibitive toxicity becomes possible.

Competing Intellectual Property

Exparel is a liposomal-encapsulated bupivacaine first released in 2012. Its unique formulation touted peripheral nerve block analgesia lasting 3 days, and has been an improvement in nonopioid analgesia after surgery. However, its performance in this role has proven less than its claims, most blocks only lasting 36 to 48 hours.

Exparel utilizes an encompassing liposome shell of varying thickness as a time-release mechanism for its encysted bupivacaine upon injection in peripheral nerve blocks. This liposomal shell is digested over time before releasing its encapsulated bupivacaine. Varying thickness of the shell allows for variable release of the local anesthetic. This allows a timed release of bupivacaine to prolong the peripheral nerve block for an advertised 72 hours of analgesia after a surgical procedure. While Exparel is somewhat effective analgesic for periods less than 48 hours, this mechanism has severe limitations extending this block to 72 hours as notable fragility has resulted in premature delivery of its bupivacaine load under certain conditions, sometimes unexpectedly. Complete prevention of Local Anesthetic Systemic Toxicity (LAST) thus has not been achieved with Exparel's full vial dose of 250 mg of bupivacaine.

Even with its shortcomings, Exparel has made important inroads in achieving increased analgesia after surgery, but still proves insufficient to provide 120 hours of post-operative analgesia needed to minimize or eliminate the need for opioid-based analgesics.

Abrahmsohn's IP is plagued by multiple defects. Specifically, Abrahmsohn specifies temporal and positional separation of the injection of any anion (HCO3) from the injection of any local anesthetic. This has the effect of decreasing the reaction between $NaHCO_3$ and ALALA drug to create the ALALA-carbonate precipitate. As this precipitate is the mechanism by which extended analgesia from surgical pain is accomplished, Abrahmsohn's methodology is insufficient to provide maximal and reliable analgesia after a surgical procedure, nor reach extended analgesic periods beyond 72-hours. This is why Abrahmsohn's block times were not consistent and varied largely as listed to be between 0.5 and 72 hours.

The method of the present invention requires, in most instances, precision placement of the block needle under ultrasound guidance against, but not penetrating, the target nerve before the ALALA-carbonate/steroid nerve block is delivered in vivo. This provides the closest delivery of the solutions to the target nerve which form the ALALA-carbonate and ALALA-steroid precipitates in and around the target nerve and result in post-operative analgesia greater than 120-hours reliably and reproducibly for surgical patients.

The anesthetic nerve block 98 interrupts the electrical potential of a nerve 12 and relieves pain within a living organism 10. As shown in FIGS. 1-16, the nerve 12 includes epineurium 14, a perineurium 16, endoneurium 18, node of Ranvier 20, myelin sheath 22, axon 24, neuron cell body 30, neuron nucleus 32, dendrites 34, axon terminals 36, oligodendrocyte (Schwann cell) 38, wrappings of myelin 40, microtubule 42, microfilaments 44, myelinated neuron (A-delta fiber) 50, peripheral terminals 52, nerve membrane (axolemma) 54 and unmyelinated neuron (C-Fiber)60.

The axon 24 is covered by the nerve membrane 54. The anesthetic nerve block 98 comprises a dispenser 102 including a storage body 104, a transfer body 106 and a tip 108 for positioning adjacent to the nerve 12. A local short acting anesthetic 76 is in the storage body 104. A physiologic carbonate base 78 is in the storage body 104. The local short acting anesthetic 76 and the physiologic carbonate base 78 are dispensed from the tip 108 of the dispenser 102 where the local short acting anesthetic 76 facilities the penetration of the physiologic carbonate base 78 through the nerve membrane 54 and into the axon 24. A local long acting anesthetic 80 is in the storage body 104. The local long acting anesthetic 80 is dispensed from the tip 108 of the dispenser 102 and penetrates through the nerve membrane 54 and into the axon 24. The local long acting anesthetic 80 and the physiologic carbonate base 78 cause a precipitate and forming a crystallization compound 82 for creating a prolonged local nerve block 99.

As shown in FIG. 17, the dispenser 102 may include an anesthetic serial injection system 100. The anesthetic serial injection system 100 includes a syringe 110 having a barrel 112 slidably receiving a plunger 114 and dispensing through a needle 116. The dispenser 102 may include a plurality of barrel membranes 118 maintain the separation of the local short acting anesthetic 76, the physiologic carbonate base 78 and the local long acting anesthetic 80 within the barrel 112.

A saline solution 84 may be positioned within the barrel 112. The plurality of barrel membranes 118 maintain the saline solution 84 between the physiologic carbonate base 78 and the local long acting anesthetic 80 within the barrel 112. The saline solution 84 cleanses the needle 116 after the local short acting anesthetic 76 and the physiologic carbonate base 78 have been dispensed from the needle 116. A goring needle 120 may be positioned internal to the barrel 112 for sequentially rupturing the plurality of barrel membranes 118 upon the depression of the plunger 114 and permitting the solutions to exit the barrel 112.

Figure 18:
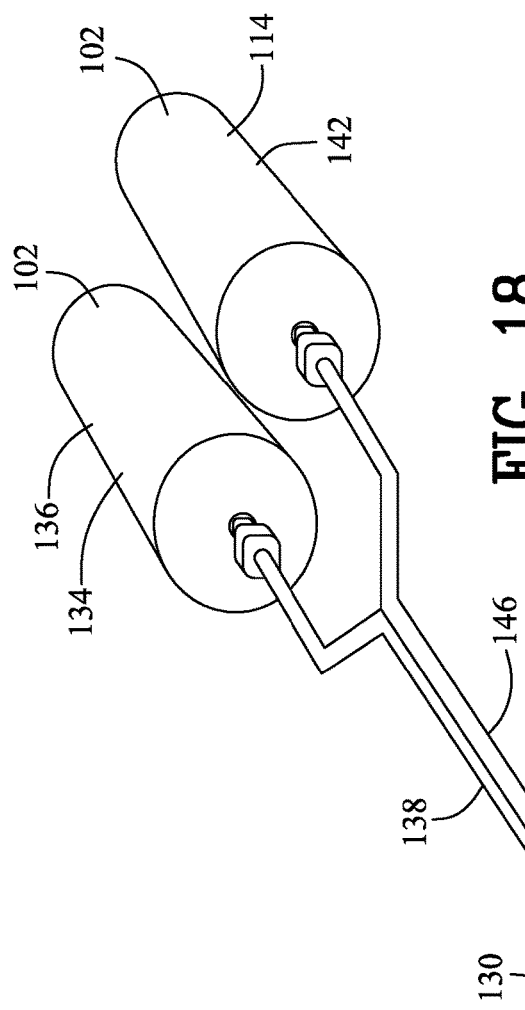
FIG. 18 is a side view of a second embodiment of the dispenser for dispensing the anesthetic nerve block solution.
Figure 19:
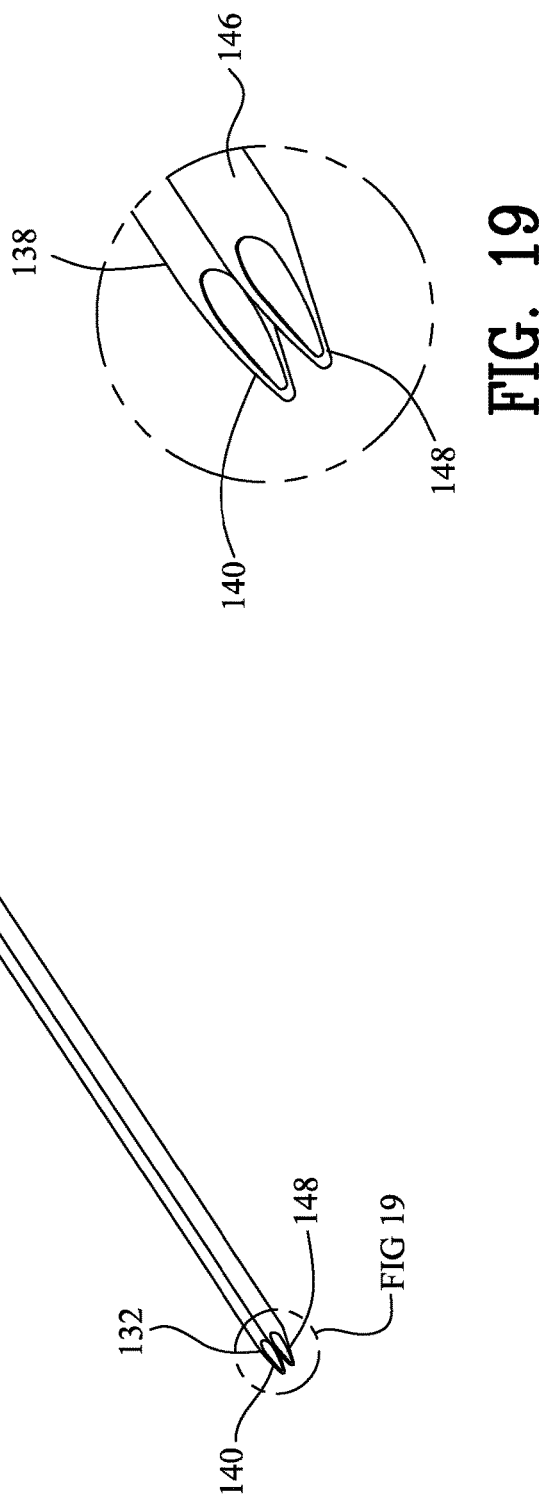
FIG. 19 is an enlarged portion of FIG. 18.

As shown in FIGS. 18 and 19, the dispenser 102 may alternatively include a first dispenser 134 and a second dispenser 142. The first dispenser 134 has a first storage body 136, a first transfer body 138 and a first tip 140 for dispensing the local short acting anesthetic 76 and the physiologic carbonate base 78. The second dispenser 142 has a second storage body 144, a second transfer body 146 and a second tip 148 for dispensing the long-acting local anesthetic or local long acting anesthetic 80. The dispenser 102 may include a coaxial needle or co-joined needles 130 for parallel injection. The co-joined needles 130 have common outlets at tips 132 where mixing of separate lumens occurs at the tip 108 of the needle 116.

As shown in FIGS. 20 and 21, the dispenser 102 may include the transfer body 106 having a bisecting transfer wall 150. The bisecting transfer wall 150 defines and separates a primary transfer body 152 from a secondary transfer body 154. The primary transfer body 152 dispenses the local short acting anesthetic 76 and the physiologic carbonate base 78. The secondary transfer body 154 dispenses the local long acting anesthetic 80. The bisecting transfer body 150 prevents mixing of the fluids except at the tip 108.

Figure 22:
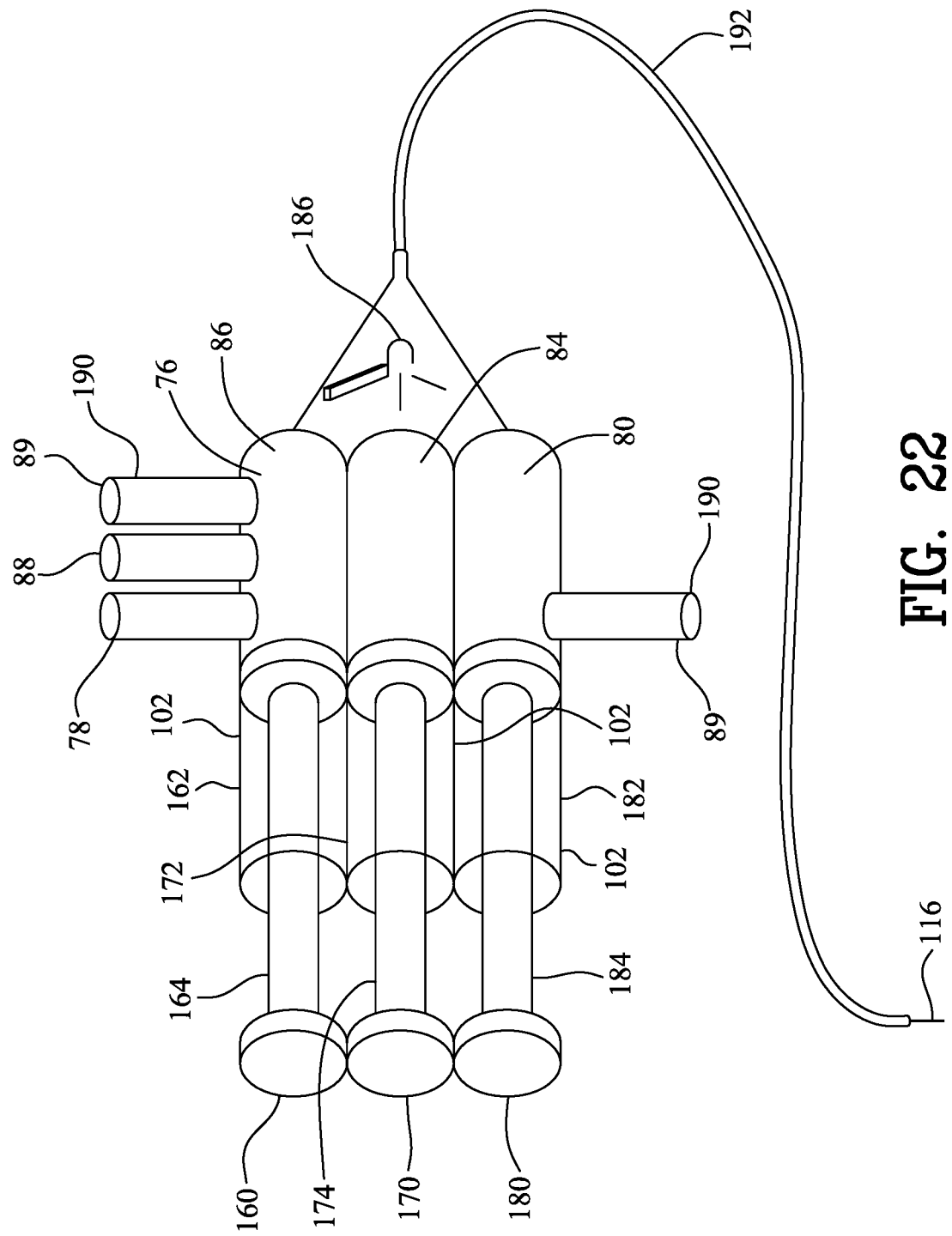
FIG. 22 is a side view of a fourth embodiment of the dispenser for dispensing the anesthetic nerve block solution.

As shown in FIG. 22, the dispenser 102 may include a first syringe 160, a second syringe 170 and a third syringe 180. The first syringe 160 has a first barrel 162 slidably receiving a first plunger 164. The first barrel 162 houses the local short acting anesthetic 76 and the physiologic carbonate base 78. The second syringe 170 has a second barrel 172 slidably receiving a second plunger 174. The second barrel 172 houses a saline solution 84. The third syringe 180 has a third barrel 182 slidably receiving a third plunger 184. The third barrel 182 houses the local long acting anesthetic 80. A stopcock 186 couples the first barrel 162, the second barrel 172 and the third barrel 182 with a needle 116. The stopcock 186 sequentially is positioned to dispense the local short acting anesthetic 76 and the physiologic carbonate base 78, the saline solution 84 and the local long acting anesthetic 80. The saline solution 84 cleanses the needle 116 after the local short acting anesthetic 76 and the physiologic carbonate base 78 have been dispensed from the needle 116. A tubing 188 may be positioned between the stopcock 186 and the needle 116. Side cylinders 190 may be coupled to the first syringe 160, the second syringe 170 and/or the third syringe 180 to dispense adjuvant(s) 89 such as additional physiologic carbonate base 78, steroids 88, epinephrine 86, and the local long acting anesthetic 80.

By combining the local short acting anesthetic 76 with the physiologic carbonate base 78 results in the pH of the local short acting anesthetic 76 increasing and alters the local short acting anesthetic 76 to unprotonated (−) molecules for more easily positioning the local short acting anesthetic 76 and the physiologic carbonate base 78 through the nerve membrane 54 and into the axon 24. The physiologic carbonate base 78 pH level determines the quantity of precipitate and crystal size in the crystallization compound 82. The physiologic carbonate base 78 mass/concentration level can be increased for raising the pH to provide a higher pH in the final mixture and resulting in a longer duration nerve block. Alternatively, the physiologic carbonate base 78 mass/concentration level can be decreased for lowering the pH to provide a lower pH in the final mixture and resulting in a shorter duration nerve block. The physiologic carbonate base 78 mass/concentration level adjustment defines a variable nerve block period of time. The physiologic carbonate base 78 mass/concentration level adjustment further defines a variable nerve block density.

The local short acting anesthetic 76 may include lidocaine. The local long acting anesthetic 80 may include bupivacaine, levo-bupivacaine, ropivacaine and tetracaine. The physiologic carbonate base 78 may include sodium bicarbonate, sodium carbonate, and sodium hydroxide.

The anesthetic nerve block 98 may further include or alternately include a steroid 88 in the storage body 104. The steroid 88 may include dexa-methasone, beta-methasone and triamcinolone and other adjuvants. The local short acting anesthetic 76 and the steroid 88 are dispensed from the tip 108 of the dispenser 102 where the local short acting anesthetic 76 facilities the penetration of the steroid 88 through the nerve membrane 54 and into the axon 24. The local long acting anesthetic 80 is in the storage body 104. The local long acting anesthetic 80 is dispensed from the tip 108 of the dispenser 102 and penetrates through the nerve membrane 54 and into the axon 24. The local long acting anesthetic 80 and the steroid 88 cause a precipitate and forming a crystallization compound 82 for creating a prolonged local nerve block 99.

As shown in FIG. 23, the method incorporating the subject invention includes creating an anesthetic nerve block 98. The anesthetic nerve block 98 interrupts the electrical potential 56 of a nerve 12 and relieves pain within a living organism 10. The method comprising the steps of dispensing a local short acting anesthetic 76 from a dispenser 102 for positioning the local short acting anesthetic 76 adjacent to the nerve 12. A physiologic carbonate base 78 is dispensed from a dispenser 102 for positioning the physiologic carbonate base 78 adjacent to the nerve 12 where the local short acting anesthetic 76 facilities the penetration of the physiologic carbonate base 78 through the nerve membrane 54 and into the axon 24. A local long acting anesthetic 80 is dispensed from a dispenser 102 for positioning the local long acting anesthetic 80 adjacent to the nerve 12 where the local long acting anesthetic 80 penetrates through the nerve membrane 54 and into the axon 24 and the local long acting anesthetic 80 and the physiologic carbonate base 78 cause a precipitate and form a crystallization compound 82 for creating a prolonged local nerve block 99.

The method may further include the step of dispensing epinephrine 86 from a dispenser 102 for determining any intravascular leakage. The method may further including the step of dispensing a saline solution 84 for cleansing the dispenser 102. The method may further include the step of dispensing a steroid 88 from a dispenser 102 for improving the precipitation and the forming of the crystallization compound 82 for creating a prolonged local nerve block 99.

As shown in FIG. 24, the subject invention may incorporate alternatively the method comprising the steps of dispensing a local short acting anesthetic 76 from a dispenser 102 for positioning the local short acting anesthetic 76 adjacent to the nerve 12. A local long acting anesthetic 80 is dispensed from a dispenser 102 for positioning the local long acting anesthetic 80 adjacent to the nerve 12. A physiologic carbonate base 78 is dispensed from a dispenser 102 for positioning the physiologic carbonate base 78 adjacent to the nerve 12 where the local short acting anesthetic 76 facilites the penetration of the physiologic carbonate base 78 through the nerve membrane 54 and into the axon 24 and where the local long acting anesthetic 80 penetrates through the nerve membrane 54 and into the axon 24 and the local long acting anesthetic 80 and the physiologic carbonate base 78 cause a precipitate and form a crystallization compound 82 for creating a prolonged local nerve block 99.

The method may further include the step of dispensing epinephrine 14 from a dispenser 102 for determining any intravascular leakage. The method may further include the step of dispensing a saline solution 84 for cleansing the dispenser 102. The method may further include the step of dispensing a steroid 88 from a dispenser 102 for improving the precipitation and the forming of the crystallization compound 82 for creating a prolonged local nerve block 99.

The subject invention method can be further illustrated below.

1. A method of creating a long-lasting nerve block in vivo by combining an amide long acting local anesthetic (ALALA) with a physiologic base in the immediate proximity of the target nerve.
   a. The long-lasting nerve block of #1 where precision placement of the block needle adjacent but not penetrating the target nerve is achieved. Currently this is achieved by ultrasound-guided blockade procedures.
   b. The nerve block of #1. where the local anesthetic is of the ALALA class includes bupivacaine, levo-bupivacaine, and ropivacaine.
   c. The nerve block of #1. where the ALALA-drug is precipitated by the physiologic base $NaHCO_3$ and whose pH may be modified by the inclusion of $Na_2CO_3$ and/or $NaOH$ to achieve a higher target pH in the injectate and final compound.
   d. The nerve block of #1 where the ALALA drug is precipitated by steroids, especially corticosteroids such as dexamethasone and betamethasone to form ALALA-steroid precipitates.
   e. The nerve block of 1. where sequential or simultaneous injections of physiologic base and ALALA-class drugs creates ALALA-carbonate precipitates and crystals.
   f. These ALALA carbonate precipitates and crystals and ALALA steroid precipitates are created as deposits in and around the axons and cell bodies of the neurons.
   g. The ALALA steroid precipitates of 1c. decompose over time first into unprotonated ALALA (−) capable of penetrating the axolemma, then into protonated ALALA(+) inside the axon which incapacitates the sodium-potassium pump and thereby blocks nerve transmission of pain impulses.
   h. The ALALA-carbonate precipitate/crystals of 1d. decompose over time first into unprotonated ALALA (−) capable of penetrating the axolemma, then into protonated ALALA(+) inside the axon which incapacitates the sodium-potassium pump and thereby blocks nerve transmission of pain impulses.
   i. The ALALA-steroid precipitate/crystals of 1c. where this decomposition of the ALALA-steroid precipitate and crystals to active ALALA drug will supply 120 hours of analgesia duration or more for the patient.
   j. The ALALA-carbonate precipitate/crystals of 1d. Where this decomposition of the ALALA-carbonate precipitate and crystals to active ALALA drug exceeds 120 hours of analgesia duration for the patient.

2. The block method of #1 where a short-acting amide local anesthetic (ALA such a lidocaine) is first combined with a physiologic base to form unprotonated ALA(−).
   a. ALA drug, such as lidocaine, utilized in solution #1 must not precipitate in alkaline solutions with a pH<10 (lidocaine precipitates at pH~1.5).
   b. The block method of #2 which, when injected through a block needle in precise proximity to the target nerve, readily penetrates the axolemma of the target nerve and brings the physiologic base with it into the neuron (cell body and axon) thereof, causing the axon's internal milieu to become alkaline.
   c. The injectate of #2 which may also contain adjuvants to augment and enhance the density and longevity of impulse blockage through that target nerve, thus blocking it for longer analgesia.
      i. The injectate of #2b always includes epinephrine or similar drug capable of notably raising pulse rate if minute quantities leak into the vascular system as a marker of significant vascular penetration. Epinephrine acts as an early warning of inadvertent vascular connection presenting the danger of LAST if injection of ALALA-drugs proceeds afterward. This is taken as an indication to abort the ALALA-carbonate block at this site at this point,
      ii. The injectate of #2b which may includes $\alpha^2$-agonists such a dexmedetomidine, clonidine, etc. to prolong and intensify the density of the resultant nerve block,
      iii. The injectate of #2b which may include steroids, especially corticosteroids, capable of causing ALALA-drugs to precipitate and so creating a separate depot of ALALA-precipitate from the ALALA carbonate precipitate/crystals. These two depots together augmenting nerve block density and longevity to create the longest-lasting sensory nerve block,
      iv. The injectate of #2b which may include an appropriate non-steroidal anti inflammatory drug (NSAID) to amplify sensory nerve blockade and aid sensory nerve block density and longevity,
      v. The injectate of #2b which may include an appropriate an N-methyl D-aspartate (NMDA) antagonist drug, such as ketamine derivatives, dextromethorphan, and others, to amplify sensory nerve blockade and aid sensory nerve block density and longevity,
      vi. The injectate of #2b which may include an opioid $\mu^2$-agonist, such as morphine, hydromorphone, meperidine, fentanyl and derivatives, etc., if opioid $\mu^2$-receptors on these specific target nerves become identified.

3. An injection of a clearing solution to clear a single-lumen needle of the alkaline solution of #2 before a subsequent injection of an ALALA-drug that could cause an immediate precipitation of ALALA-carbonate within that lumen and subsequent lumen blockade that prevents full injection of the desired ALALA dose.
   a. This clearing solution is needed only in single-lumen needles and catheters in which both injectates (Solutions 1 and 2) must pass through the same needle lumen.
   b. Bifid-lumen needles do not allow mixing of these solutions except at the distal tip in close proximity to the target nerve where precipitates cannot plug the bifid needle. Thus a clearing solution is unnecessary for bifid needles and bifid delivery catheters.

4. A mandatory 2-minute wait (test dose) is imposed between the injection of Solution #1 before Solution #2 is given to ensure Local Anesthetic Systemic Toxicity (LAST) does not occur. This is done by listening to the pulse-oximeter and/or watching the EKG tracing (or similar objective indicator of pulse rate) for a tachycardia at least 15% above baseline (115% of baseline) pulse which can indicate leakage of Solution #1 intravascularly because of inadvertent penetration of a blood vessel during block needle placement. This is a potent indicator the block should be aborted at that site. If Solution #2 is then injected after a positive tachycardia result, the patient may experience seizure, cardiac arrhythmias, cardiac arrest, and death.

5. The block of #1 wherein, after #3's clearing solution as needed to neutralize intralumenal pH of the needle (from Solution #1) and the 2-minute wait to prevent LAST of #4 is performed, a second injectate of an ALALA-drug (Solution #2) is depositied perineurally through the block needle to mix with the physiologic base in and around the nerve (especially intra-axonally) to create the ALALA-carbonate precipitate and crystals.

6. Adjuvants may be distributed between Solutions #1 and 2, depending on their stability in an alkaline solution.

a. Only epinephrine must be included in Solution #1 with the ALA-drug as a precaution against LAST.

b. Steroid adjuvants must also be delivered in Solution #1 as they react with ALALA drugs to form precipitates. These adjuvants may be delivered separately from the physiologic bases because of stability issues between the steroids and physiologic bases.

c. If necessary, Solution #1 may be divided into separate injection for ALA (such a lidocaine) and physiologic base so as to preserve the integrity of epinephrine in Solution #1.

d. As necessary or desired, all other compatible adjuvants may be moved to Solution #2.

7. Control of nerve block duration is by the quantity of ALALA-carbonate precipitate/crystals formed.

a. This is controlled by pH of physiologic base concentrations in Solution 1 with greater pH converting a greater percentage of the ALALA drug to ALALA carbonate precipitates/crystals when mixed with Solution #2.

b. Final target pH of the mixture of Solutions #1 and #2 is a pH<8.4.

c. A pH>8.0 in Solution #1 may be necessary, depending on stability of adjuvants, in single-lumen block needles to adequately control formation of ALALA-carbonate precipitates/crystals at the target nerve site.

d. In bifid-lumen needles, catheters, and similar delivery devices, much higher nonphysiologic concentrations of physiologic bases may be used in solution #1 so long as final mixing of Solutions 1 and 2 still results in physiologic pH<8.4 for the final ALALA-carbonate precipitate deposited.

8. Creation of a titrable duration of nerve block can be accomplished by varying the mass of ALALA-carbonate precipitate/crystals formed by varying the pH of the Solution #1 and the choice and mass of steroid(s) in Solution #1. This results in a variable duration of nerve blockade with the two different precipitates (ALALA-carbonate and ALALA steroid) having different decomposition times and different conversion times back to ALALA(+) intra-axonally for nerve blockade.

9. This same methodology for amide local anesthetics can also be applied to ester local anesthetics as tetracaine has a pKAeven higher than bupivacaine and will for tetracainecarbonate and tetracaine-steroid precipitates even more readily. But tetracaine is an ester local anesthetic which breaks down to para-amino benzoic acid (PABA), a known irritant and allergen in minute quantities, and capable of causing anaphylaxis in the larger drug masses anticipated in these extended blocks with analgesic durations greater than 72-120 hours. Because of this danger, tetracaine should be avoided currently in these extended blocks, but will be claimed in this IP on the possibility safer derivatives of tetracaine will be discovered in the future without PABA or other allergen formation.

Realizing that the injection of local anesthetics in and around surgical sites for pain relief is and has been the normal hospital protocol for many years and the desire for longer lasting local anesthesia has also been a sought-after goal during that time. The current invention, ALALA compound, has been able to meet that goal by extending the local anesthesia efficacy period to 5 days and beyond.

The current invention, ALALA compound, is administered just as the current local anesthetics are administered. Following the current toxicity steps in the existing hospital protocol the ALALA compound is merely substituted in the same step as currently utilized local anesthetics are introduced. The Only departure from the existing hospital protocol is that our ALALA compound is introduced into the equation as a perineural block instead of an epidural block. Also note that all components of our novel ALALA compound are currently FDA approved.

LIST OF REFERENCE SIGNS 10 living organism
12 sciatic nerve
14 epineurium
16 perineurium
18 endoneurium
20 node of Ranvier
22 myelin sheath
24 axon
30 neuron cell body
32 neuron nucleus
34 dendrites
36 axon terminals
38 oligodendrocyte (Schwann cell)
40 wrappings of myelin
42 microtubule
44 microfilaments
50 myelinated neuron (A-delta fiber)
52 peripheral terminals (such as skin)
54 nerve membrane (axolenima)
56 action potential
58 stimulus
60 unmyelinated neuron (C-Fiber)
70 unprotonated lidocaine
72 protonated lidocaine
74 bicarbonate $HCO_3$
76 local short acting anesthetic: lidocaine
78 physiologic carbonate base: sodium bicarbonate, sodium carbonate, sodium hydroxide, dexa-methasone, beta-methasone and triamcinolone: (plus possible Adjuvants)
80 local long acting anesthetic: bupivacaine, levo-bupivacaine, ropivacaine, tetracaine (ALALA)
82 (ALALA) carbonate forming precipitate
84 saline solution
86 epinephrine
88 steroid
89 adjuvants
90 Nodes of Ranvier with extra-axonal deposits of bupivacaine carbonate precipitate crystallizing
92 bupivacaine $HCO_3$
94 bupivacaine++OH— +$CO_2$
96 bupivacaine-+$H_2O$+$CO_2$
98 anesthetic nerve block
99 prolonged local nerve block/ALALA-carbonate precipitate/ALALA steroid precipitate
100 anesthetic serial injection system
102 dispenser 104 storage body
106 transfer body
108 tip
110 syringe
112 barrel
114 plunger
116 needle
118 plurality of barrel membranes for separation
120 goring needle to rupture membranes
130 coaxial needle for parallel injection
132 co-joined needles with common outlets at tips where mixing of separate lumens occurs at the tip of the catheter.
134 first dispenser
136 first storage body
138 first transfer body
140 first tip
142 second dispenser
144 second storage body
146 second transfer body
148 second tip
150 bisecting transfer wall prevents mixing of fluids except at tip
152 primary transfer body
154 secondary transfer body
160 first syringe
162 first barrel
164 first plunger
170 second syringe
172 second barrel
174 second plunger
180 third syringe
182 third barrel
184 third plunger
186 stopcock-four-way sequential valve
188 tubing
190 adjuvant side cylinders for a steroid and or physiologic carbonate base which may be used as precipitating agent for ALALA The present disclosure includes that contained in the appended claims as well as the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An anesthetic nerve block for interrupting the electrical potential of a nerve and relieving pain within a living organism, the nerve having an axon covered by a nerve membrane, the anesthetic nerve block, comprising:
a dispenser including a storage body, a transfer body and a tip for positioning adjacent to the nerve;
a local short acting anesthetic in said storage body;
a physiologic carbonate base in said storage body;
said local short acting anesthetic and said physiologic carbonate base dispensed from said tip of said dispenser where said local short acting anesthetic facilities the penetration of said physiologic carbonate base through the nerve membrane and into the axon;
a local long acting anesthetic in said storage body;
said local long acting anesthetic dispensed from said tip of said dispenser and penetrating through the nerve membrane and into the axon; and
said local long acting anesthetic and said physiologic carbonate base causing a precipitate and forming a crystallization compound for creating a prolonged local nerve block.

2. The anesthetic nerve block as set forth in claim 1, wherein said dispenser includes a syringe having a barrel slidably receiving a plunger and dispensing through a needle.

3. The anesthetic nerve block as set forth in claim 2, further including a plurality of barrel membranes for maintaining the separation of said local short acting anesthetic, said physiologic carbonate base and said local long acting anesthetic within said barrel.

4. The anesthetic nerve block as set forth in claim 3, further including a saline solution in said barrel;
said plurality of barrel membranes maintaining said saline solution between said physiologic carbonate base and said local long acting anesthetic within said barrel; and
said saline solution cleansing said needle after said local short acting anesthetic and said physiologic carbonate base have been dispensed from said needle.

5. The anesthetic nerve block as set forth in claim 1, wherein said dispenser includes a first dispenser and a second dispenser;
said first dispenser having a first storage body, a first transfer body and a first tip for dispensing said local short acting anesthetic and said physiologic carbonate base; and
said second dispenser having a second storage body, a second transfer body and a second tip for dispensing said local long acting anesthetic.

6. The anesthetic nerve block as set forth in claim 1, wherein said storage body includes a first storage body and a second storage body communicating with said transfer body;
said transfer body includes a bisecting transfer body;
said bisecting transfer body defining a primary transfer body and a secondary transfer body;
said primary transfer body dispensing said local short acting anesthetic and said physiologic carbonate base; and
said secondary transfer body dispensing said local long acting anesthetic.

7. The anesthetic nerve block as set forth in claim 1, wherein said dispenser includes a first syringe, a second syringe and a third syringe;
said first syringe having a first barrel slidably receiving a first plunger;
said first barrel housing said local short acting anesthetic and said physiologic carbonate base;
said second syringe having a second barrel slidably receiving a second plunger;
said second barrel housing a saline solution;
said third syringe having a third barrel slidably receiving a third plunger;
said third barrel housing said local long acting anesthetic;
a stopcock coupling said first barrel, said second barrel and said third barrel with a needle;
said stopcock sequentially positioned to dispense said local short acting anesthetic and said physiologic carbonate base, said saline solution and said local long acting anesthetic; and
said saline solution cleansing said needle after said local short acting anesthetic and said physiologic carbonate base have been dispensed from said needle.

8. The anesthetic nerve block as set forth in claim 1, wherein said combining said local short acting anesthetic with said physiologic carbonate base results in the pH of said local short acting anesthetic increasing and alters said local short acting anesthetic to unprotonated (−) molecules for more easily positioning said local short acting anesthetic and said physiologic carbonate base through the nerve membrane and into the axon;

said physiologic carbonate base pH level determining the quantity of precipitate and crystal size in said crystallization compound;

said physiologic carbonate base mass/concentration level increased for raising the pH to provide a higher pH in the final mixture;

said physiologic carbonate base mass/concentration level adjustment defining a variable nerve block period of time; and said physiologic carbonate base mass/concentration level adjustment defining a variable nerve block density.

9. The anesthetic nerve block as set forth in claim 1, wherein said local short acting anesthetic is lidocaine.

10. The anesthetic nerve block as set forth in claim 1, wherein said local long acting anesthetic is selected from the group consisting of bupivacaine, levo-bupivacaine, ropivacaine and tetracaine.

11. The anesthetic nerve block as set forth in claim 1, wherein said physiologic carbonate base is selected from the group consisting of sodium bicarbonate, sodium carbonate, and sodium hydroxide.

12. The anesthetic nerve block as set forth in claim 1, further including a steroid in said storage body;

said local long acting anesthetic and said steroid causing said precipitate and forming said crystallization compound for creating said prolonged local nerve block; and said steroid is selected from the group consisting of dexa-methasone, beta-methasone and triamcinolone.

13. An anesthetic nerve block for interrupting the electrical potential of a nerve and relieving pain within a living organism, the nerve having an axon covered by a nerve membrane, the anesthetic nerve block, comprising:

a dispenser including a storage body, a dispenser body and a tip for positioning adjacent to the nerve;

a local short acting anesthetic in said storage body;

a steroid said storage body;

said local short acting anesthetic and said steroid dispensed from said tip of said dispenser where said local short acting anesthetic facilities the penetration of said steroid through the nerve membrane and into the axon;

a local long acting anesthetic in said storage body;

said local long acting anesthetic dispensed from said tip of said dispenser and penetrating through the nerve membrane and into the axon; and said local long acting anesthetic and said steroid causing a precipitate and forming a crystallization compound for creating a prolonged local nerve block.

14. The anesthetic nerve block as set forth in claim 13, wherein said steroid is selected from the group consisting of dexa-methasone, beta-methasone and triamcinolone.

15. A method for creating an anesthetic nerve block, the anesthetic nerve block interrupting the electrical potential of a nerve and relieving pain within a living organism, the nerve having an axon covered by a nerve membrane, the method comprising the steps of:

dispensing a local short acting anesthetic from a dispenser for positioning the local short acting anesthetic adjacent to the nerve;

dispensing a physiologic carbonate base from a dispenser for positioning the physiologic carbonate base adjacent to the nerve where the local short acting anesthetic facilities the penetration of the physiologic carbonate base through the nerve membrane and into the axon; and dispensing a local long acting anesthetic from a dispenser for positioning the local long acting anesthetic adjacent to the nerve where the local long acting anesthetic penetrates through the nerve membrane and into the axon and the local long acting anesthetic and the physiologic carbonate base cause a precipitate and form a crystallization compound for creating a prolonged local nerve block.

16. The method for creating an anesthetic nerve block as set forth in claim 15, further including the step of dispensing epinephrine from a dispenser for determining any intravascular leakage.

17. The method for creating an anesthetic nerve block as set forth in claim 15, further including the step of dispensing a saline solution for cleansing the dispenser.

18. The method for creating an anesthetic nerve block as set forth in claim 15, further including the step of dispensing steroid from a dispenser for improving the precipitation and the forming of the crystallization compound for creating a prolonged local nerve block.

19. A method for creating an anesthetic nerve block, the anesthetic nerve block interrupting the electrical potential of a nerve and relieving pain within a living organism, the nerve having an axon covered by a nerve membrane, the method comprising the steps of:

dispensing a local short acting anesthetic from a dispenser for positioning the local short acting anesthetic adjacent to the nerve;

dispensing a local long acting anesthetic from a dispenser for positioning the local long acting anesthetic adjacent to the nerve; and dispensing a physiologic carbonate base from a dispenser for positioning the physiologic carbonate base adjacent to the nerve where the local short acting anesthetic facilities the penetration of the physiologic carbonate base through the nerve membrane and into the axon and where the local long acting anesthetic penetrates through the nerve membrane and into the axon and the local long acting anesthetic and the physiologic carbonate base cause a precipitate and form a crystallization compound for creating a prolonged local nerve block.

20. The method for creating an anesthetic nerve block as set forth in claim 19, further including the step of dispensing epinephrine from a dispenser for determining any intravascular leakage.

21. The method for creating an anesthetic nerve block as set forth in claim 19, further including the step of dispensing a saline solution for cleansing the dispenser.

22. The method for creating an anesthetic nerve block as set forth in claim 19, further including the step of dispensing steroid from a dispenser for improving the precipitation and the forming of the crystallization compound for creating a prolonged local nerve block.

\* \* \* \* \*